(12) United States Patent
Clark et al.

(10) Patent No.: US 6,502,463 B1
(45) Date of Patent: Jan. 7, 2003

(54) ULTRASONIC STRAIN GAGE USING A MOTORIZED ELECTROMAGNETIC ACOUSTIC TRANSDUCER

(75) Inventors: Alfred V. Clark, Boulder, CO (US); George Alers, Boulder, CO (US); Thanh Nguyen, Roancke, VA (US); Christopher Hehman, Belmont, MA (US); Kevin Coakley, Boulder, CO (US)

(73) Assignee: The United States of America as represented by the Secretary of Commerce, Washington, DC (US)

( * ) Notice: Subject to any disclaimer, the term of this patent is extended or adjusted under 35 U.S.C. 154(b) by 0 days.

(21) Appl. No.: 09/942,359

(22) Filed: Aug. 29, 2001

Related U.S. Application Data

(62) Division of application No. 09/274,538, filed on Mar. 23, 1999, now Pat. No. 6,311,558.
(60) Provisional application No. 60/079,053, filed on Mar. 23, 1998.

(51) Int. Cl.$^7$ ............................................... G01N 29/18
(52) U.S. Cl. ........................................... 73/643; 73/597
(58) Field of Search ........................ 73/643, 622, 661, 73/632, 597, 602, 609, 600

(56) References Cited

U.S. PATENT DOCUMENTS

| | | | |
|---|---|---|---|
| 4,295,214 A | 10/1981 | Thompson | 367/140 |
| 4,466,287 A | 8/1984 | Repplinger et al. | 73/643 |
| 4,522,071 A | 6/1985 | Thompson | 73/597 |
| 5,050,703 A | 9/1991 | Graff et al. | 181/106 |
| 5,115,681 A | 5/1992 | Bouheraoua et al. | 73/801 |
| 5,164,921 A | 11/1992 | Graff et al. | 367/140 |
| 5,237,874 A | 8/1993 | Latimer et al. | 73/621 |
| 5,299,458 A | 4/1994 | Clark, Jr. et al. | 73/597 |
| 5,467,655 A | 11/1995 | Hyoguchi et al. | 73/579 |
| 5,537,876 A | 7/1996 | Davidson et al. | 73/624 |
| 5,608,691 A | 3/1997 | MacLauchlan et al. | 367/140 |
| 5,619,423 A | 4/1997 | Scrantz | 364/507 |
| 5,652,389 A | 7/1997 | Schaps et al. | 73/643 |
| 5,675,087 A | 10/1997 | MacLauchlan et al. | 73/761 |
| 5,714,688 A | 2/1998 | Buttram et al. | 73/597 |
| 5,750,900 A * | 5/1998 | Hugentobler et al. | 73/779 |
| 5,777,230 A * | 7/1998 | Vandervalk | 73/632 |
| 5,804,727 A * | 9/1998 | Lu et al. | 73/597 |
| 5,808,201 A * | 9/1998 | Hugentobler | 73/643 |
| 5,811,682 A * | 9/1998 | Ohtani et al. | 73/643 |
| 5,813,280 A | 9/1998 | Johnson et al. | 73/643 |
| 5,979,241 A * | 11/1999 | Vandervalk | 73/644 |
| 6,122,968 A * | 9/2000 | Vandervalk | 73/597 |
| 6,155,117 A * | 12/2000 | Stevens et al. | 73/643 |
| 6,250,160 B1 * | 6/2001 | Koch et al. | 73/602 |
| 6,282,962 B1 * | 9/2001 | Koch et al. | 73/602 |
| 6,311,558 B1 * | 11/2001 | Clark et al. | 73/643 |

* cited by examiner

*Primary Examiner*—Hezron Williams
*Assistant Examiner*—Jacques M Saint-Surin
(74) *Attorney, Agent, or Firm*—Rick Martin; Patent Law Offices of Rick Martin, P.C.

(57) ABSTRACT

A method and apparatus for measurement of stress in a specimen utilizing a motorized electromagnetic acoustic transducer (EMAT). Stress causes a rotation of the pure-mode polarization directions of SH-waves and a change in the phase of waves polarized along these certain directions. The method utilizes a rotating small-aperture EMAT, connected to a processor, to measure phase and amplitude data as a function of angle. The EMAT is placed on a workpiece at the location where the stress is to be measured. The acoustic birefringence B is determined from the normalized difference of these phases. From these data, an algorithm calculates values of B and Φ. The workpiece is then stressed or its stress state is changed. The values are measured again at the same location. Stress is determined from the change in B and Φ.

12 Claims, 19 Drawing Sheets

CROSS-SECTION OF EMAT

CROSS-SECTION OF MOTORIZED EMAT

ULTRASONIC STRAIN GAGE USING A MOTORIZED ELECTROMAGNETIC ACOUSTIC TRANSDUCER

REFERENCE TO RELATED APPLICATIONS

This divisional application claims priority from U.S. Provisional Application serial No. 60/079,053 filed Mar. 23, 1998, which was allowed in application Ser. No. 09/274,538, filed Mar. 23, 1999, and issued U.S. Pat. No. 6,311,558 on Nov. 6, 2001.

FIELD OF THE INVENTION

The field of the present invention relates to electromagnetic acoustic transducers (EMAT), more particularly, to rotating EMAT'S used as strain gages.

BACKGROUND OF THE INVENTION

In non-destructive testing using EMAT's, it is preferable for the stressed region to be struck by the incident wave at an angle of 90 degrees. This requires the EMAT to be oriented, data collected, then re-oriented for the next series of measurements. This practice involves large amounts of time in manually orienting and re-orienting the EMAT. The prior art does not allow for the rapid collection and analysis of data for calculation of stress in a specimen.

Further, the prior art involved measurement of signals on a specimen at a particular point in time. The measurements reflected certain characteristics of the specimen at the time the measurements were taken. Characteristics detected primarily included defects and flaws. Real time detection of the stress state of a specimen was not available.

Representative of the art is:

U.S. Pat. No. 5,813,280 (1998) to Johnson et al. discloses a force sensor including a cylindrical body having a central section and two distal sections wherein selected acoustic resonant modes are trapped in the central section and decays exponentially in the distal sections possibly using an electromechanical acoustic transducer (EMAT) to excite and detect the selected resonant modes in the central section.

U.S. Pat. No. 5,808,201 (1998) to Hugentobler discloses an improved electromagnetic acoustic transducer (EMAT) for monitoring uniaxially applied stress in an underlying workpiece.

U.S. Pat. No. 5,750,900 (1998) to Hugentobler et al. discloses an improved strain gauge and a method of using an electromagnetic acoustic transducer (EMAT) for monitoring stress and strain in an underlying workpiece.

U.S. Pat. No. 5,652,389 (1997) to Schapes et al. discloses a method and apparatus for the non-contact inspection of workpieces having a plate-like portion of the first part joined via an inertia weld to the end of a second part extending away from the plate-like portion.

U.S. Pat. No. 5,299,458 (1994) to Clark, Jr. et al. discloses an indication of the formability of metallic sheet which is determined using a correlation between nondestructively measurable ultrasonic properties and a formability index.

U.S. Pat. No. 5,115,681 (1992) to Bouheraoua et al. discloses a two-step method of studying the acoustic response of a piece by recording signals with acoustic sensors.

U.S. Pat. No. 5,811,682 (1998) to Ohtani et al. discloses an electromagnetic acoustic transducer for magnets and a sheet type coil unit.

U.S. Pat. No. 5,804,727 (1998) to Lu et al. discloses a method for determining and evaluating physical characteristics of a material.

U.S. Pat. No. 5,714,688 (1998) to Buttram et al. discloses a method of examining a ductile iron casting to determine a percent of nodularity present in the casting using an electromagnetic acoustic transducer (EMAT) system to determine a time-of-flight of an ultrasonic shear wave pulse transmitted through the casting at a selected location from which a velocity of sound in the casting can be determined.

U.S. Pat. No. 5,675,087 (1997) to MacLauchlan et al. discloses a device for measuring a load on a part and for monitoring the integrity of the part such as a bolt, comprises a socket having walls defining an interior space wherein the socket engages the bolt for transmitting a load to the bolt.

U.S. Pat. No. 5,619,423 (1997) to Scrantz discloses an improved system, method, and apparatus for the external ultrasonic inspection of fluidized tubulars and tanks.

U.S. Pat. No. 5,608,691 (1997) to MacLauchlan et al. discloses a shield for an electromagnetic acoustic transducer (EMAT) has multiple layers of electrically insulating and electrically conductive materials which contain a coil of the EMAT.

U.S. Pat. No. 5,537,876 (1996) to Davidson et al. discloses an apparatus and method for nondestructive evaluation for detection of flaws in butt welds in steel sheets using horizontal shear ultrasonic waves generated on the surface thereof.

U.S. Pat. No. 5,467,655 (1995) to Hyoguchi et al. discloses a method and apparatus for measuring properties of a cold-rolled thin steel sheet, comprising an electromagnetic ultrasonic wave device, a computing device, and a controlling device for executing the measurement of properties and the computation.

U.S. Pat. No. 5,237,874 (1993) to Latimer et al. discloses a method and apparatus of non-destructive testing wherein a generally bi-directional wave-generating electromagnetic acoustic transducer is pivotally mounted upon a base with this transducer being continuously rotated or oscillated upon the base as it is moved with respect to the workpiece (or the workpiece is moved with respect to the base).

U.S. Pat. No. 5,164,921 (1992) to Graff et al. discloses an electrodynamic permanent magnet transducer for the non-destructive testing of workpieces by means of ultrasound.

U.S. Pat. No. 5,050,703 (1991) to Graff et al. discloses an electrodynamic transducer head for a non-destructive testing of workpieces with electrically conductive surfaces by way of ultrasound.

U.S. Pat. No. 4,522,071 (1985) to Thompson discloses a method and apparatus for determining stress in a material independent of micro-structural variation and anisotropy's.

U.S. Pat. No. 4,466,287 (1984) to Repplinger et al. discloses a method for non-contact, non-destructive testing of a test body of ferromagnetic and/or electrically-conductive material with ultrasound waves.

U.S. Pat. No. 4,295,214 (1981) to Thompson discloses an electromagnetic acoustic transducer, including an electrical conductor adapted to carry an alternating current in a current plane.

What is needed is a rotating EMAT, connected to a processor, that can be rotated through 360 degrees. What is needed is a rotating EMAT connected to a processor using an algorithm to calculate birefringence from the normalized differences in the phase of SH waves in a specimen. What is needed is a rotating EMAT connected to a processor using an algorithm to calculate the pure-mode polarization directions of SH waves in a specimen. What is needed is a rotating EMAT connected to a processor using an algorithm to calculate the stress in a specimen. What is needed is a rotating EMAT connected to a processor used as a strain gage.

SUMMARY OF THE INVENTION

The primary aspect of the present invention is to provide a rotating EMAT, connected to a processor, that can be rotated through 360 degrees.

Another aspect of the present invention is to provide a rotating EMAT connected to a processor using an algorithm to calculate birefringence from the normalized differences in the phase of SH waves in a specimen.

Another aspect of the present invention is to provide a rotating EMAT connected to a processor using an algorithm to calculate the pure-mode polarization directions of SH waves in a specimen.

Another aspect of the present invention is to provide a rotating EMAT connected to a processor using an algorithm to calculate the stress in a specimen.

Another aspect of the present invention is to provide a rotating EMAT connected to a processor used as a strain gage.

Other aspects of this invention will appear from the following description and appended claims, reference being made to the accompanying drawings forming a part of this specification wherein like reference characters designate corresponding parts in the several views.

The invention comprises an EMAT connected to a processor. The EMAT rotates about a central axis while collecting data on a specimen. The invention is used to measure the change in plane stress in metallic components (e.g. rolled plates of steel and aluminum). In the absence of stress, the pure-mode polarization directions of SH-waves in these components are the rolling and transverse directions. The velocity of a wave polarized in the rolling directions generally exceeds that of a wave polarized in the transverse direction due to anisotropy induced by rolling (which causes preferential alignment of the grains). With the transducer polarized at an arbitrary angle the wave "splits" into components polarized along the rolling and transverse directions. Each component propagates with its own velocity. These components recombine along the transducer polarization direction and interfere. Consider now the case of applied plane stress, having components $\sigma_{xx}$, $\sigma_{yy}$ and $\sigma_{xy}$. Because of the stresses there will be two effects, first, the orientation of pure-mode polarization directions may change, second, the velocity or time of flight (TOF) of waves polarized along these directions will change.

In the absence of stress the rolling and transverse directions typically are pure-mode polarization directions for SH-waves. It is convenient to refer stresses to a coordinate system parallel to these axes: see FIG. 2. In general the principal stress directions are not coincident with these axes, and a rotation of the pure mode directions through angle $\Phi$ results: see FIG. 5.

The relation between $\Phi$ and stress is given by:

$$\tan 2\Phi = \{2m\ \Phi_{xy}\}/\{B_o + m\ (\sigma_{yy} - \sigma_{xx})\} \tag{1}$$

where m is the acoustoelastic constant and $B_o$ is the birefringence in the unstressed state. The birefringence is defined by $$B = (V_f - V_s)/V_{ave} \tag{2}$$

where $V_f$ is the velocity of the faster wave, $V_s$ is the slower wave velocity and $V_{ave}$ is their average. The birefringence is related to stress by:

$$B^2 = [B_o + m\ (\sigma_{yy} - \sigma_{xx})]^2 + [2m\sigma_{xy}]^2 \tag{3}$$

Eqns. (1) and (3) can be combined (using trigonometric identities) to give:

$$B \cos 2\Phi - B_o = m\ (\sigma_{yy} - \sigma_{xx}) \tag{4}$$

and $$B \sin 2\Phi = 2m\sigma_{xy} \tag{5}$$

Most applications of the acoustic birefringence method to date have used eqn. (4). That is measurements are made where the principal stress direction is coincident with the rolling and transverse directions, so that (see eqn. (1)), either $\Phi = 0$ or $\Phi = \pi/2$. Problems arise when the texture is not homogenous so that variations in $B_o$ occur. These variations result in artifacts in stress measurement and if large enough, can give rise to errors larger than the stresses to be determined.

In contrast eqn. (5) shows that measurement of the shear stress $\sigma k$ is independent of texture. By determining gradients of shear stress and using the stress-equilibrium equations it is possible in principle to determine the normal stresses $\sigma_{yy}$ and $\sigma_{xx}$.

To determine stress we require that correct values of B and $\Phi$ be obtained. Therefore we seek to determine model with the minimum number of parameters necessary to obtain accurate stress measurements from our ultrasonic data.

This model is implemented in interactive software: to query the operator for inputs; produce graphs to compare data and the fit based on our model. In its current form this algorithm runs on a personal computer with a processor clock rate of 100 MHz. Running the algorithm requires less than 30 s from the time phase data is imported, until the values of B and $\Phi$ are calculated.

Comparison of Model Predictions and Experiment

Amplitude and Phase for Arbitrary Orientation of EMAT

Consider the case shown in FIG. 5, where the EMAT is oriented at an angle $\theta$ to the X and Y-axes. (These are the pure-mode polarization directions in the stressed state.) These axes are rotated by angle $\Phi$ from the pure-mode polarization directions in the unstressed state ($X_o$-$Y_o$ axes). Hence the EMAT is oriented at angle $\eta$ to the $X_o$-axis; $\eta = \theta + \Phi$.

The EMAT detects the particle velocity. The expression for the particle velocity $u_n$ in the $n_{th}$ echo is:

$$u_n = A^* \exp\{j(\omega t - P_s)\} + B^* \exp\{j(\omega t - P_f)\} \tag{6}$$

Here $P_s$ is the phase of the component polarized along the X-axis ("slow" direction) and $P_f$ is the corresponding phase of the component polarized along the Y-axis ("fast" direction). $\omega$ is the frequency (in radians) of the toneburst used to excite the EMAT. Denote d to be twice the specimen thickness. For an acoustic pathlength of nd, the phase is $P_s = \omega nd/V_s$ for the slow wave component.

The coefficients A* and B* give the contributions of the components polarized along the X- and Y- axes, respectively:

$$A^* = U \exp(-\alpha_s nd) \cos^2\theta \tag{7}$$

$$B^* = U \exp(-\alpha_f nd) \sin^2\theta \tag{8}$$

Here U is the amplitude of the particle velocity generated by the EMAT at the specimen surface; $\alpha_s$ and $\alpha_f$ are the attenuation coefficients for the "slow" and "fast" waves.

For simplicity we suppress the exp (jωt) dependence. The expression for the particle velocity can be written as a phasor with amplitude $a_n$ $$a_n(\theta; \Delta P_n) = \{A^{*2} + B^{*2} + 2A^*B^* \cos(P_s - P_f)\}^{1/2} \tag{9}$$

and phase $P_n$ $$P_n = \tan^{-1}\{(A^* \sin P_s + B^* \sin P_f)/(A^* \cos P_s + B^* \cos P_f)\} \tag{10}$$

Effect of Texture and Stress: 3-parameter Model

Now consider the special case $\alpha_s = \alpha_f$. That is, we assume the attenuation is the same for components polarized in the slow and fast directions. We rewrite the expressions for amplitude and phase in forms to show more clearly the effect of interference between these components. We denote $\Delta P_n = (P_s - P_f)$ as the difference in phase between the slow and fast wave components in the $n_{th}$ echo.

$$a_n(\theta; \Delta P_n) = U \exp(-\alpha nd)\{1 - \sin^2\theta \sin^2(\Delta P_n/2)\}^{1/2} \tag{11}$$

The phase is now given by $P_n = (P_{a,n} + \psi_n)$. Here $P_{a,n}$ is the average phase in the echo (the phase for no birefringence), and $\psi_n$ is the additional phase due to interference between fast and slow wave components:

$$\psi_n(\theta; \Delta P_n) = \tan^{-1}\{\tan(\Delta P_n/2) \cos 2\theta\}. \tag{12}$$

We used a commercial instrument which recorded both amplitude and phase data as our EMAT rotated. The instrument, under computer control, produced a file of relative amplitude data as a function of "clock time", t. Data collection was started so that t=0 when η=0; that is, with the EMAT oriented along the transverse direction (see FIG. 2). The EMAT is rotated with constant angular velocity Ω. Since η=Ωt, we generated a data file with relative amplitude and phase as dependent variables and EMAT orientation η as the independent variable.

The relative amplitude $A_R$ is given by:

$$A_R(\theta; \Delta P_n) = 20 \log_{10}\{a(\theta; \Delta P_n)/a(\theta; \Delta P_n)\} \tag{13}$$

FIG. 20 shows the theoretical behavior of $A_R$ for different values of $\Delta P_n$. Note that maxima occur for θ=0°, 90°, etc.; that is, with the EMAT oriented along the slow and fast directions. The minima occur at θ=45°,135°, etc.; now the EMAT is oriented midway between slow and fast directions. The minima become more pronounced as $\Delta P_n$ approaches 180°.

The behavior of the additional phase term $\psi_n(\theta; \Delta P_n)$ is shown in FIG. 21. For small differences in phase between fast and slow wave components, $\psi_n$ behaves sinusoidally. As the difference approaches 180°, the phase term behaves like a square wave.

To determine Φ, the algorithm first calculates "synthetic data" $\psi_n^{syn}$ $$\psi_n^{syn}(\eta - \Phi^*; \Delta P_n) = \tan^{-1}\{\tan(0.5[P_s - P_f])\cos 2(\eta - \Phi^*)\} \tag{14}$$

where Φ* is an assumed value for Φ (recall that θ=η−Φ). The algorithm next calculates the difference between the data, and values predicted from eqn. (14), for each value of η. The phase prediction errors are squared and summed to give the sum of squared residuals, for the assumed value of Φ.

The estimate of Φ is constrained to fall in the interval (0,π). The best estimate of Φ is determined by minimizing the sum of the squared phase residuals.

This method gives good results for measurements made on an aluminum shrink-fit specimen with a large EMAT. In this case both the relative amplitude and phase data behaved as predicted by eqn. (11) and (13). However, for the small EMAT, discrepancies occurred such as those shown in FIGS. 22 and 23.

For the relative amplitude data the local maxima are not of equal magnitude. This indicates that the attenuation is not the same for waves polarized along the fast and slow directions. The local minima are also of unequal magnitude. This implies that the minima do not repeat when the EMAT rotates by 180°.

Likewise the phase data does not repeat under 180° rotation of the EMAT. This would imply that rotating the EMAT by 180° somehow changes the velocity, which is nonphysical. In addition the rate of change of phase with rotation appears to have asymmetry, another result not in agreement with the 3-parameter model predictions.

Effect of Differential Attenuation: 4-parameter Model

To improve the agreement between model predictions and experiment, we assumed that the attenuation in the fast and slow waves is different. Differential attenuation can be quantified by the parameter $\Delta A_n$: $\Delta A_n = [\exp(-\alpha_f nd) - \exp(-\alpha_s nd)]/2$. If $\Delta A_n > 0$, the attenuation in the slow wave is larger; if $\Delta A_n < 0$ the attenuation in the fast wave is larger.

This model predicts that the local maxima of the relative amplitude still occur for the fast and slow directions, when $\Delta P_n$ is approximately equal to an odd multiple of π. However if $\Delta A_n > 0$, $A_R$ will be larger for the fast direction and vice versa. This is in qualitative agreement with the data of FIG. 22.

The model also predicts that the local minima will be shifted from θ=π/4, 3π/4, etc. to θ=π/4−$\Delta A_n$/2, 3π/4+$\Delta A_n$/2, etc.[8]. Hence if $\Delta A_n > 0$, the model predicts that maximum interference between the fast and slow wave components no longer occurs with the EMAT oriented midway between the fast and slow directions. Since the slow wave component is smaller, the maximum interference occurs with the EMAT oriented closer to the slow direction by $\Delta A_n$/2 radians.

The 4-parameter model predicts shifts in the zeroes of the additional phase $\psi_n$ from θ=π/4, 3π/4,etc. (halfway between slow and fast directions) to θ=π/4−$\Delta A_n$/2, 3π/4+$\Delta A_n$/2,etc. The locations of maxima and minima in $\psi_n$ remain the same as in the 3-parameter fit.

A nonlinear least squares fitting routine was used to implement the 4-parameter model. Since the 4-parameter model can account for the difference in local maxima of $A_R$ it improved the agreement with relative amplitude data. Since it cannot account for differences in measured $\psi_n$ under 180° rotation it did not significantly improve the fit to phase data.

Inhomogeneity in Velocity and Attenuation—10 Parameter Model

In this case it is assumed that the center of the EMAT aperture is not coincident with the center of rotation. A simple model of EMAT transduction is used to show that the EMAT output voltage is proportional to the particle velocity at the center of the aperture. An instrument is used which measures phase and amplitude of the output voltage. Hence the aperture center.

Assume that the center of the aperture is offset an amount $r_o$ from the center of rotation, and at an angle $\alpha$ to the EMAT polarization direction. Consider a coordinate system with origin at the center of rotation and axes parallel to the $X_o$- and $Y_o$- directions. In this coordinate system the coordinates of the aperture center are $(r_o \cos(\eta+\alpha), r_o \sin(\eta+\alpha))$.

Assume that the velocities of the slow and fast waves are inhomogeneous. Then for example the slow velocity $V_s$ can be expanded in a (truncated) Taylor series:

$$V_s (r_o \cos \eta, r_o \sin \eta) = V_s (0,0) + (\partial V_s/\partial X_o) r_o \cos (\eta+\alpha) + (\partial V_s/\partial Y_o) r_o \sin (\eta+\alpha). \quad (15)$$

Since $P_s = \omega nd/V_s$, we model the slow phase as follows:

$$P_{s,m} = \gamma_2 + \gamma_5 \cos \eta + \gamma_6 \sin \eta \quad (16)$$

Here $P_{s,m}$ is the measured phase and $\gamma_2$ is the correct phase (phase at the center of rotation). A similar expression can be written for $P_f$:

$$P_{f,m} = \gamma_3 + \gamma_7 \cos \eta + \gamma_8 \sin \eta \quad (17)$$

$\Delta P_n$ is given by $\gamma_2 - \gamma_3$; that is, $\Delta P_n$ is the value of $P_{s,m} - P_{f,m}$ averaged over $0 \leq \eta \leq 2\pi$.

In like fashion we account for inhomogeneity in differential attenuation by rewriting eqn. (7) as $$A^* = (\gamma_4 + \gamma_9 \cos \eta + \gamma_{100} \sin \eta) \cos^2 (\eta - \gamma_1), \quad (18)$$

where we use $\theta = \eta - \Phi$, and let $\Phi = \gamma_1$. For example, $\gamma_4$ is the value of $\exp(-(\alpha_s - \alpha_f)nd)$ at the center of rotation. The same procedure which leads to eqn. (18) also gives $B^* = \sin^2(\eta - \gamma_1)$.

From the above we see that this model requires a total of 10 parameters (6 for phase; 3 for attenuation; 1 for $\Phi$).

Improved agreement was found between model predictions and the phase data; see FIG. 24. The agreement between predicted and measured relative amplitude also improved, but to a lesser degree.

Effect of Varying Transducer Gain With Rotation: 13-parameter Model

In this model we kept the same functional forms for $A^*$, $B^*$, and the phase $\psi_n$. However we now assumed that the amplitude is given by $$a(\theta;\Delta P_n) = \{f(\eta) [A^{*2} + B^{*2} + 2A^*B^* \cos(P_s - P_f)]\}^{1/2} \quad (19)$$

where $$f(\eta) = \gamma_{11} + \gamma_{12} \cos \eta + \gamma_{13} \sin \eta \quad (20)$$

The term $f(\eta)$ allows for variation in apparent transducer gain as the EMAT rotates.

The predicted phase, based on 13-parameter model, is now almost indistinguishable from the phase data. There was also improvement in the fit to the amplitude data using this model; see FIG. 25.

Using Method to Determine Changes in Stress

The relation between the stress changes and changes in (weighted) time-of-flight (TOF's) is given by:

$$\Delta \sigma_{xx} = K_{11} \Delta \tau_1 + K_{12} \Delta \tau_2 \quad (21)$$

$$\Delta \sigma_{yy} = K_{21} \Delta \tau_1 + K_{22} \Delta \tau_2$$

$$\Delta \sigma_{xy} = K_{33} \Delta \tau_3$$

Here we define:

$$\tau_1 = (T_s \cos^2 \Phi + T_f \sin^2 \Phi)/T_o \quad (22)$$

$$\tau_2 = (T_f \cos^2 \Phi + T_s \sin^2 \Phi)/T_o$$

$$\tau_3 = [(T_s - T_f) \sin 2\Phi]/2T_o.$$

$\Phi$ is the angle between the pure-mode directions ("acoustic axes") in the unstressed and stressed states (see FIG. 2). $T_s$ is the TOF of the wave polarized along the "slow" direction (X-axis) and $T_f$ is the corresponding TOF in the "fast" direction (Y-axis); To is the average TOF. The K's are acoustoelastic constants determined by performing uniaxial tension tests with specimens cut at a different angle to the specimen rolling direction. For example:

$$K_{11} = (d\tau_1/d\sigma_{xx})^{-1},$$

$$K_{12} = (d\tau_2/d\sigma_{xx})^{-1}$$

for a uniaxial specimen cut along the transverse direction. Once the K's are known (either from values in the literature or by performing the uniaxial tension tests described above), the procedure to determine stress changes proceeds as follows. The transducer is placed at selected measurement locations on the specimen in the initial state. TOFs and $\Phi$ are then measured (note: if the initial state is unstressed, then $\Phi$ is zero and it is only necessary to measure TOFs). The specimen is then stressed; at some convenient time later the EMAT is repositioned at the same locations and a new set of TOFs and $\Phi$ measured. The EMAT is used to generate and receive waves that are used to determine $\Phi$, in conjunction with either a phase-sensitive instrument or time-measuring instrument to measure TOF's. The EMAT is also used to generate and receive waves polarized along the pure-mode directions to determine the TOFs.

Values of $\tau$'s are calculated for both stressed and unstressed state, and stress changes calculated. Since the K's are large, small errors in TOFs result in large stress errors. Conversely, stress causes only small changes in TOFs. An error analysis shows that to resolve 10 MPa of stress in steel requires resolution in TOF of order of 10 ppm.

The transduction mechanism of the EMAT makes it ideal for this application. Conventional piezoelectric transducers require couplants to transmit sound from transducer to specimen. It is difficult to accurately control the couplant thickness, and special fixturing is required. In contrast EMATs generate sound directly in the surface of the specimen and can work with clearances of a few mm. Hence they can be rapidly scanned and rotated to collect the required data.

A cross-section of the EMAT shows that it consists of a "racetrack" coil, excited by a high-power toneburst by the commercial instrument. Magnets (with opposite polarity) are placed above the "straight" sides of the coil. The reaction force $F_L$ between the magnetic induction B with the induced eddy current density J is: $F_L = J \times B$. This causes a shearing force at the specimen surface, which sets up a propagating SH wave.

Implementation of the motorized, rotating EMAT is as follows. The coil and magnet are contained inside a rotating cylinder. Bearings are press-fit onto the cylinder and are seated inside the (fixed) outer case. The motor is mounted on the case and rotates the cylinder by means of a gear train. Offsetting the motor in this manner allows rotation of the EMAT without twisting the signal and power cables which connect the EMAT to the commercial instrument.

The specifications for the EMAT are: effective EMAT aperture is 25×25 mm; angular velocity =1 rpm.

Effect of Birefringence on Phase

As an example, the EMAT generates a wave polarized at angle Θ to the pure-mode polarization directions in the stressed configuration. The EMAT is polarized at a known angle η to the $X_o$-axis (the transverse direction). The wave splits into components polarized along the X,Y axes, having amplitude cos θ, sin θ, respectively. Each component of the wave propagates with a different velocity. Upon recombining the components along the transducer polarization direction, the particle velocity U is given by:

$$U^2 \sim \exp(j\,P_{ave})\{\cos^2\theta \exp(j\,\Delta P)+\sin^2\theta \exp(-j\,\Delta P)\} \quad (23)$$

Here $P_{ave}$ is the average phase and $\Delta P=P_s-P_f$ is difference in phase between velocity components polarized along slow and fast directions. The term in braces represents the effect of interference between these components. It is this term that is used to determined.

After some algebraic manipulation, this term is re-written in the form a(θ) exp(jΦ(θ)) where Φ(θ) is the additional phase resulting from interference. Φ(θ) is determined from measurements made with the phase-sensitive commercial instrument as the EMAT is rotated. We calculated $$\Phi(\theta)=\arctan\{\tan^{-1}(\Delta P/2)\cos 2\theta\}$$

Note that θ is unknown, since θ=η−Φ and Φ is unknown.

ψ(η) is then measured with the phase sensitive instrument as the EMAT is rotated. Software supplied with the instrument generates a file containing "clock time" and phase. Clock time is recorded as time since the EMAT is polarized along the transverse axis. The file is recorded on the computer hard disk for further evaluation by our algorithm.

The operator then imports the data and runs the algorithm. In the first step, clock time is converted to angle η by: η=ωt where ω is the angular velocity of the rotating EMAT. The algorithm next determines the maximum and minimum phase $\psi_{max}$ and $\psi_{min}$. The difference in phase ΔP is calculated from: $\Delta P=\psi_{max}-\psi_{min}$ From values of η and ΔP the "synthetic phase" is calculated:

$$\psi_{syn}(\eta;\Phi^*)=\arctan\{\tan^{-1}(\Delta P/2)\cos 2(\eta-\Phi^*)\}$$

Note that θ=η−Φ;here Φ* is the assumed value of Φ. For each value of Φ* (in 1° increments) in the interval between 0 and 180 degrees, the algorithm calculates the residual:

$$R(\Phi^*)=\Sigma(\psi_{syn}(\eta_i;\Phi^*)-\psi(\eta_i;\Phi^*)^2\}.$$

Here $\eta_I=\omega t_I$ where $t_I$ is the $I_{th}$ increment of clock time. The algorithm searches through values of R(Φ*) to find the minimum. The corresponding value of Φ* gives the best estimate of Φ.

The EMAT is rotated and phase data is recorded for about 80 seconds with the 1 rpm motor. The algorithm requires about 30 seconds to run from the time the phase data is imported until the correct Φ is determined.

Once Φ is determined, the EMAT is rotated so that it is polarized along, for example, the X-axis. We then measure TOF of the wave polarized along this axis with our digital gate/counter system. The operator then selects a particular cycle on a particular echo for measurement purposes. These must be the same for measurements taken in the unstressed and stressed states. This is done by manually adjusting the location (in time) of the gate such that it is in the ON state just before the zero crossing. Then a comparator circuit generates a square pulses when the zero crossing occurs. This pulse is input to the STOP channel of the counter. The counter is started by a trigger pulse from the commercial instrument. The trigger pulse is coincident with the toneburst that drives the EMAT.

The EMAT is positioned at the measurement location and is rotated; the phase data is measured and recorded by the commercial instrument; the angle Φ is determined with the algorithm. Then the EMAT is rotated along the "fast" and "slow" directions and the corresponding TOFs measured with the counter.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE PREFERRED EMBODIMENT

Figure 1:
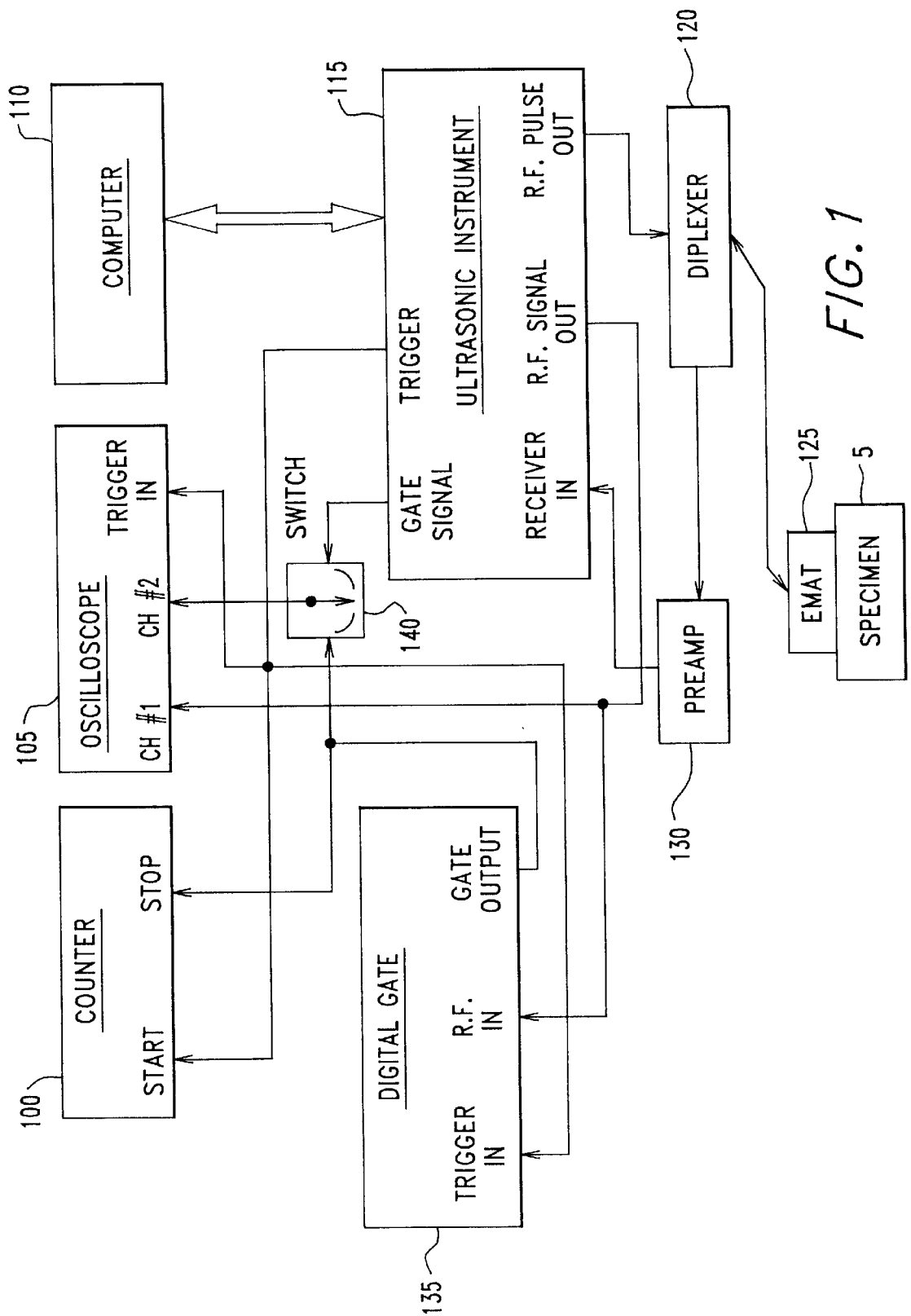
FIG. 1 is a block diagram of the hybrid system with phase instrument and counter.

A block diagram of the hybrid system of phase instrument and counter is shown in FIG. 1. Computer 110 is electrically connected to the ultrasonic instrument 115, known in the art. Ultrasonic instrument 115, known in the art, generates a series of four signals; an RF pulse to a diplexer 120, which sends a pulse to EMAT 125; an RF signal to an oscilloscope 105 channel and digital gate 135; a trigger signal to the oscilloscope, counter 100 and digital gate 135; and a gate signal to switch 140. Upon receipt of the signal from the diplexer, EMAT 125 emits an EM pulse which generates SH- waves within the specimen S. EMAT 125 then receives a signal from the specimen S, that is then transmitted to the diplexer 120. Diplexer 120 sends the signal to the preamp 130. Ultrasonic equipment 115 receives a signal from preamp 130, which signal is then sent to the digital gate and the oscilloscope. Output from the digital gate 135 is connected to counter 100. Counter 100 receives its 'start' signal from the ultrasonic instrument trigger signal and its 'stop' signal from the digital gate output signal. Digital gate 135 output is also connected to switch 140. The invention has been implemented with interactive software: to query the operator for inputs; produce graphs to compare data and the fit based on the model. The algorithm runs on a personal computer with a processor clock rate of 100 MHz, and requires 16 meg of memory. The operation of the system is described in further detail with reference to the noted figures.

The system is used to measure change in plane stress in metallic components (e.g. rolled plates of steel and aluminum). In the absence of stress, the pure-mode polarization directions of SH- waves in these components are the rolling and transverse directions. The velocity of a wave polarized in the rolling directions generally exceeds that of a wave polarized in the transverse direction due to anisotropy induced by rolling (which causes preferential alignment of the grains). With the transducer polarized at an arbitrary angle the wave "splits" into components polarized along the rolling and transverse directions. Each component propagates with its own velocity. These components recombine along the transducer polarization direction and interfere.

Figure 2:
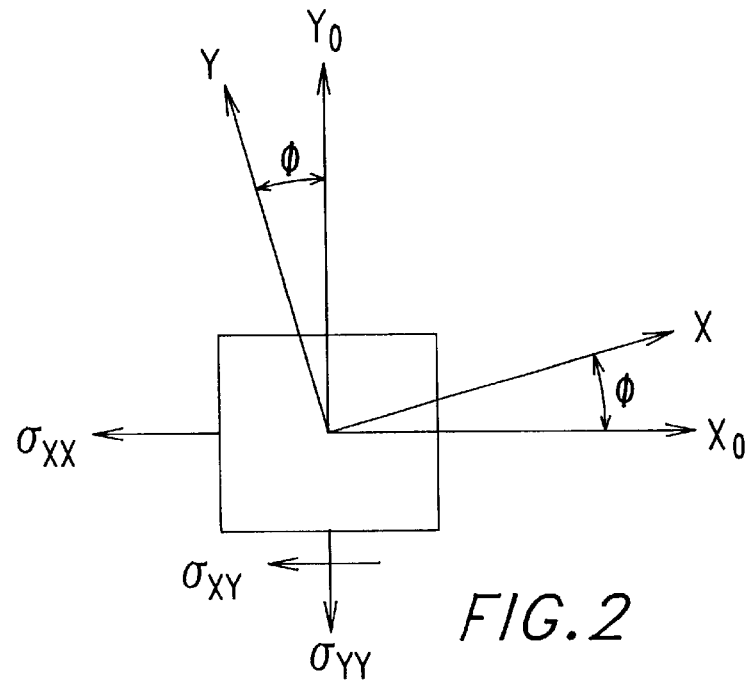
FIG. 2 shows the case of applied plane stress, having components $\sigma_{xx}$, $\sigma_{yy}$ and $\sigma_{xy}$.

FIG. 2 shows the case of applied plane stress, having components $\sigma_{xx}$, $\sigma_{yy}$ and $\sigma_{xy}$. Because of the stresses, there will be two effects, first, the orientation of pure-mode polarization directions may change, and second, the time of flight (TOF) of waves polarized along these directions will change.

The relation between $\Phi$ and stress is given by:

$$\tan 2\Phi = \{2m\ \sigma_{xy}\}/\{B_o + m\ (\sigma_{yy} - \sigma_{xx})\} \tag{24}$$

where m is the acoustoelastic constant and $B_o$ is the birefringence in the unstressed state. The birefringence is defined by $$B = (V_f - V_s)/V_{ave} \tag{25}$$

where $V_f$ is the velocity of the faster wave, $V_s$ is the slower wave velocity and $V_{ave}$ is their average. The birefringence is related to stress by:

$$B^2 = [B_o + m\ (\sigma_{yy} - \sigma_{xx})]^2 + [2m\ \sigma_{xy}]^2 \tag{26}$$

Eqns. (24) and (26) can be combined (using trigonometric identities) to give:

$$B \cos 2\Phi - B_o = m\ (\sigma_{yy} - \sigma_{xx}) \tag{27}$$

and $$B \sin 2\Phi = 2m\ \sigma_{xy} \tag{28}$$

Most applications of the acoustic birefringence method to date have used eqn. (27). That is measurements are made where the principal stress direction is coincident with the rolling and transverse directions, so that (see eqn. (24)), either $\Phi = 0$ or $\Phi = \pi/2$. Problems arise when the texture is not homogenous so that variations in $B_o$ occur. These variations result in artifacts in stress measurement and if large enough, can give rise to errors larger than the stresses to be determined.

In contrast eqn. (28) shows that measurement of the shear stress $\sigma_{xy}$ is independent of texture. By determining gradients of shear stress and using the stress-equilibrium equations it is possible in principle to determine the normal stresses $\sigma_{yy}$ and $\sigma_{xx}$.

To determine stress we require that correct values of B and $\Phi$ be obtained. Therefore we seek to determine model with the minimum number of parameters necessary to obtain accurate stress measurements from our ultrasonic data.

This model is implemented in interactive software: to query the operator for inputs; produce graphs to compare data and the fit based on our model. In its current form this algorithm runs on a personal computer with a processor clock rate of 100 MHz. Running the algorithm requires less than 30 seconds from the time phase data is imported, until the values of B and $\Phi$ are calculated.

Comparison of Model Predictions and Experiment

Amplitude and Phase for Arbitrary Orientation of EMAT

Figure 5:
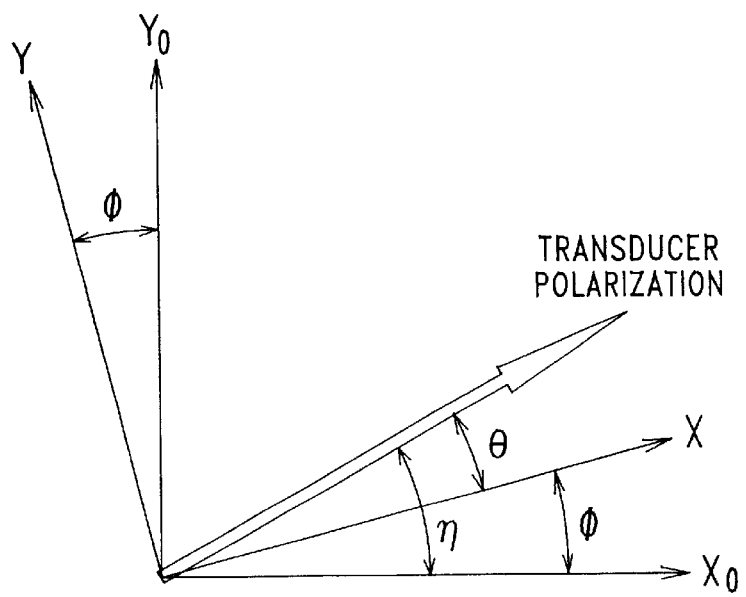
FIG. 5 shows the EMAT generating a wave polarized at angle Θ to the acoustic axes in the stressed configuration.

Consider the case shown in FIG. 5, where the EMAT is oriented at an angle $\theta$ to the acoustic axis in the stressed configuration. These are the pure-mode polarization directions in the stressed state. These axes are rotated by angle $\Phi$ from the pure-mode polarization directions in the unstressed state ($X_o$-$Y_o$ axes). Hence the EMAT is oriented at angle $\eta$ to the $X_o$-axis; $\eta = \theta + \Phi$.

The EMAT detects the particle velocity. The expression for the particle velocity $u_n$ the $n_{th}$ echo is:

$$u_n = A^* \exp\{j\ (\omega t - P_s)\} + B^* \exp\{j(\omega t - P_f)\} \tag{29}$$

Here $P_s$ is the phase of the component polarized along the X-axis ("slow" direction) and $P_f$ is the corresponding phase of the component polarized along the Y-axis ("fast" direction). $\omega$ is the frequency (in radians) of the toneburst used to excite the EMAT. Denote d to be twice the specimen thickness. For an acoustic pathlength of nd, the phase is $P_s = \omega nd/V_s$ for the slow wave component.

The coefficients $A^*$ and $B^*$ give the contributions of the components polarized along the X- and Y- axes, respectively:

$$A^* = U \exp(-\alpha_s nd) \cos^2\theta \tag{30}$$

$$B^* = U \exp(-\alpha_f nd) \sin^2\theta \tag{31}$$

Here U is the amplitude of the particle velocity generated by the EMAT at the specimen surface; $\alpha_s$ and $\alpha_f$ are the attenuation coefficients for the "slow" and "fast" waves.

For simplicity we suppress the exp (j$\omega$t)dependence. The expression for the particle velocity can be written as a phasor with amplitude $a_n$ $$a_n(\theta; \Delta - P_n) = \{A^{*2} + B^{*2} + 2A^*B^* \cos(P_s - P_f)\}^{1/2} \tag{32}$$

and phase $P_n$ $$P_n = \tan^{-1}\{(A^*\sin P_s + B^*\sin P_f)/(A^*\cos P_s + B^*\cos P_f)\} \tag{33}$$

Effect of Texture and Stress: 3-parameter Model

Now consider the special case $\alpha_s = \alpha_f$. That is, we assume the attenuation is the same for components polarized in the slow and fast directions. We rewrite the expressions for amplitude and phase in forms to show more clearly the effect of interference between these components. We denote $\Delta P_n = (P_s - P_f)$ as the difference in phase between the slow and fast wave components in the $n_{th}$ echo.

$$a_n(\theta; \Delta P_n) = U \exp(-\alpha nd)\{1 - \sin^2\theta \sin^2(\Delta P_n/2)\}^{1/2} \tag{34}$$

The phase is now given by $P_f = (P_{a,n} + \psi_n)$. Here $P_{a,n}$ is the average phase in the echo (the phase for no birefringence), and $\psi_n$ is the additional phase due to interference between fast and slow wave components:

$$\psi_n(\theta; \Delta P_n) = \tan^{-1}\{\tan(\Delta P_n/2) \cos 2\theta\}. \tag{35}$$

We used a commercial instrument which recorded both amplitude and phase data as our EMAT rotated. The instrument, under computer control, produced a file of relative amplitude data as a function of "clock time", t. Data collection was started so that t=0 when $\eta = 0$; that is, with the EMAT oriented along the transverse direction (see FIG. 2). The EMAT is rotated with constant angular velocity $\Omega$. Since $\eta = \Omega t$, we generated a data file with relative amplitude and phase as dependent variables and EMAT orientation $\eta$ as the independent variable.

The relative amplitude $A_R$ is given by:

$$A_R(\theta; \Delta P_n) = 20 \log_{10}\{a(\theta; \Delta P_n)/a(\alpha; \Delta P_n)\} \tag{36}$$

Figure 20:
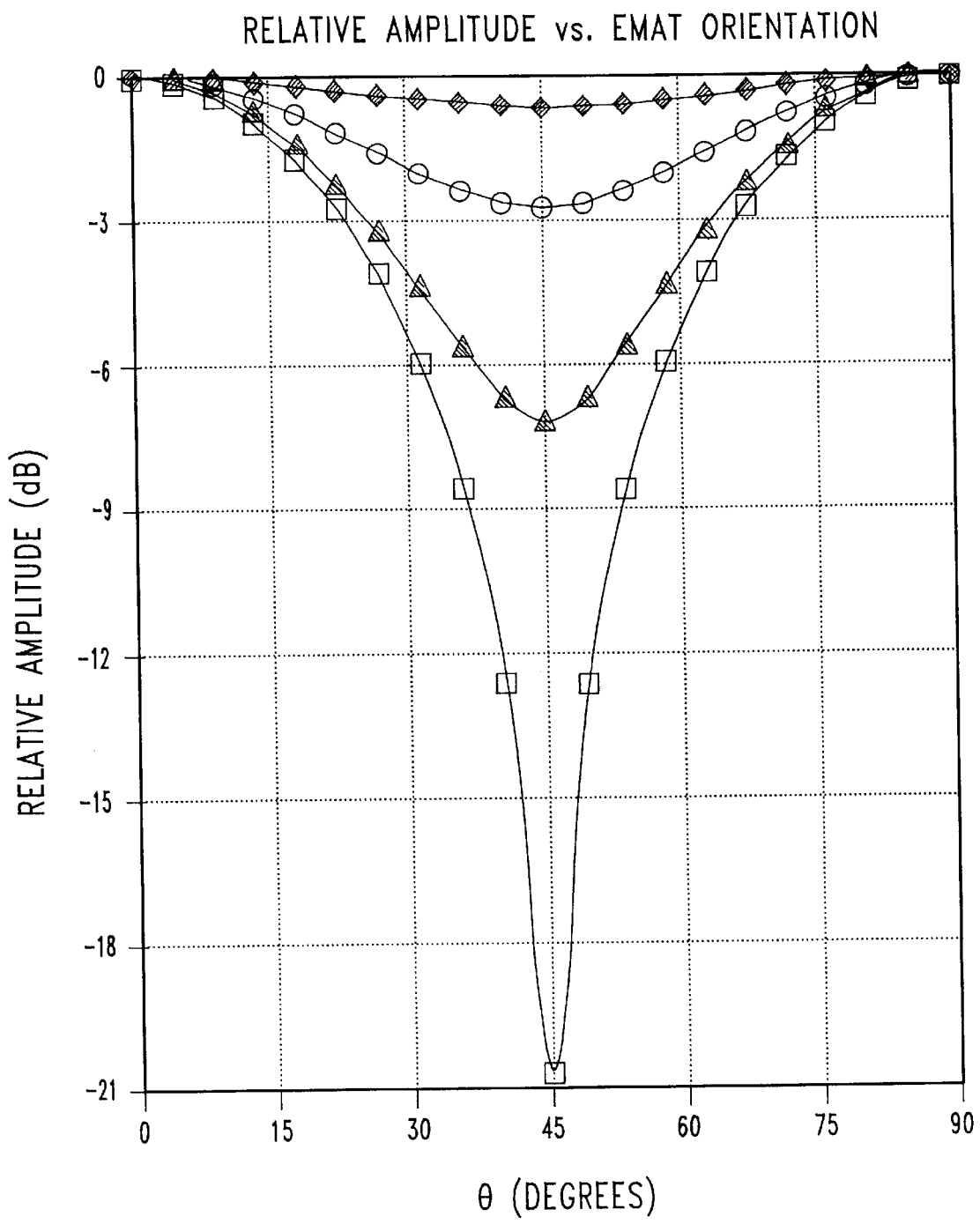
FIG. 20 is a plot of relative amplitude vrs EMAT orientation.

FIG. 20 is a plot of relative amplitude versus EMAT orientation. Note that maxima occur for $\theta = 0°, 90°$, etc.; that is, with the EMAT oriented along the slow and fast directions. The minima occur at $\theta = 45°, 135°$, etc.; now the EMAT is oriented midway between slow and fast directions. The minima become more pronounced as $\Delta P_n$ approaches 180°.

Figure 21:
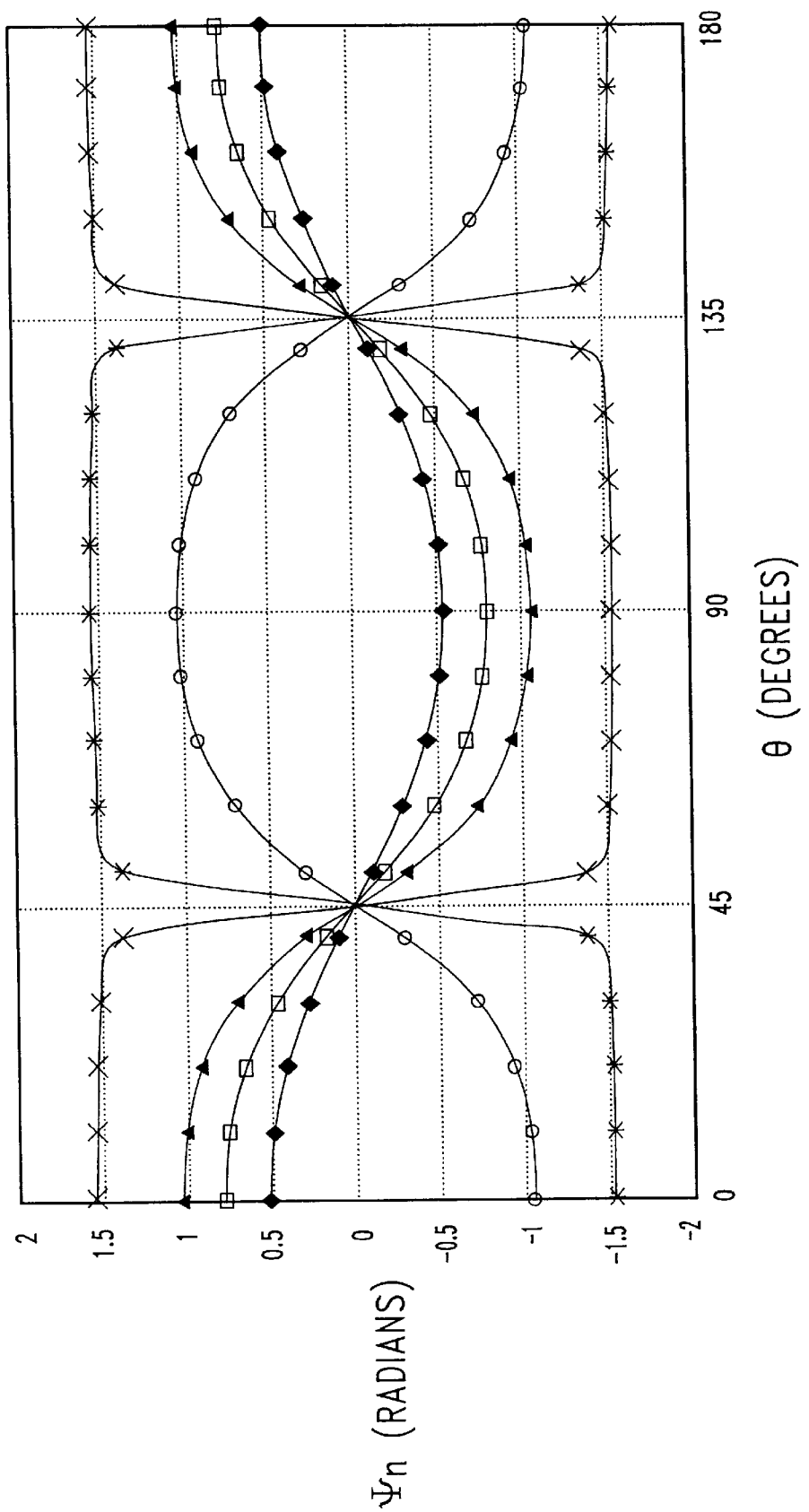
FIG. 21 is a plot of theoretical behavior of phase for various values of $\Delta P_n$.

The behavior of phase for various values of $\Delta P_n$ is shown in FIG. 21. For small differences in phase between fast and slow wave components, $\psi_n$ behaves sinusoidally. As the difference approaches 180°, the phase term behaves like a square wave.

To determine $\Phi$, the algorithm first calculates "synthetic data" $\psi_n^{syn}$ $$\psi_n^{syn}(\eta - \Phi^*; \Delta P_n) = \tan^{-1}\{\tan(0.5[P_s - P_f]\cos 2(\eta - \Phi^*)\} \tag{37}$$

where $\Phi^*$ is an assumed value for $\Phi$ (recall that $\theta = \eta - \Phi$). The algorithm next calculates the difference between the data, and values predicted from eqn. (37), for each value of $\eta$. The phase prediction errors are squared and summed to give the sum of squared residuals, for the assumed value of $\Phi$.

The estimate of $\Phi$ is constrained to fall in the interval $(0,\pi)$. The best estimate of $\Phi$ is determined by minimizing the sum of the squared phase residuals.

Figure 22:
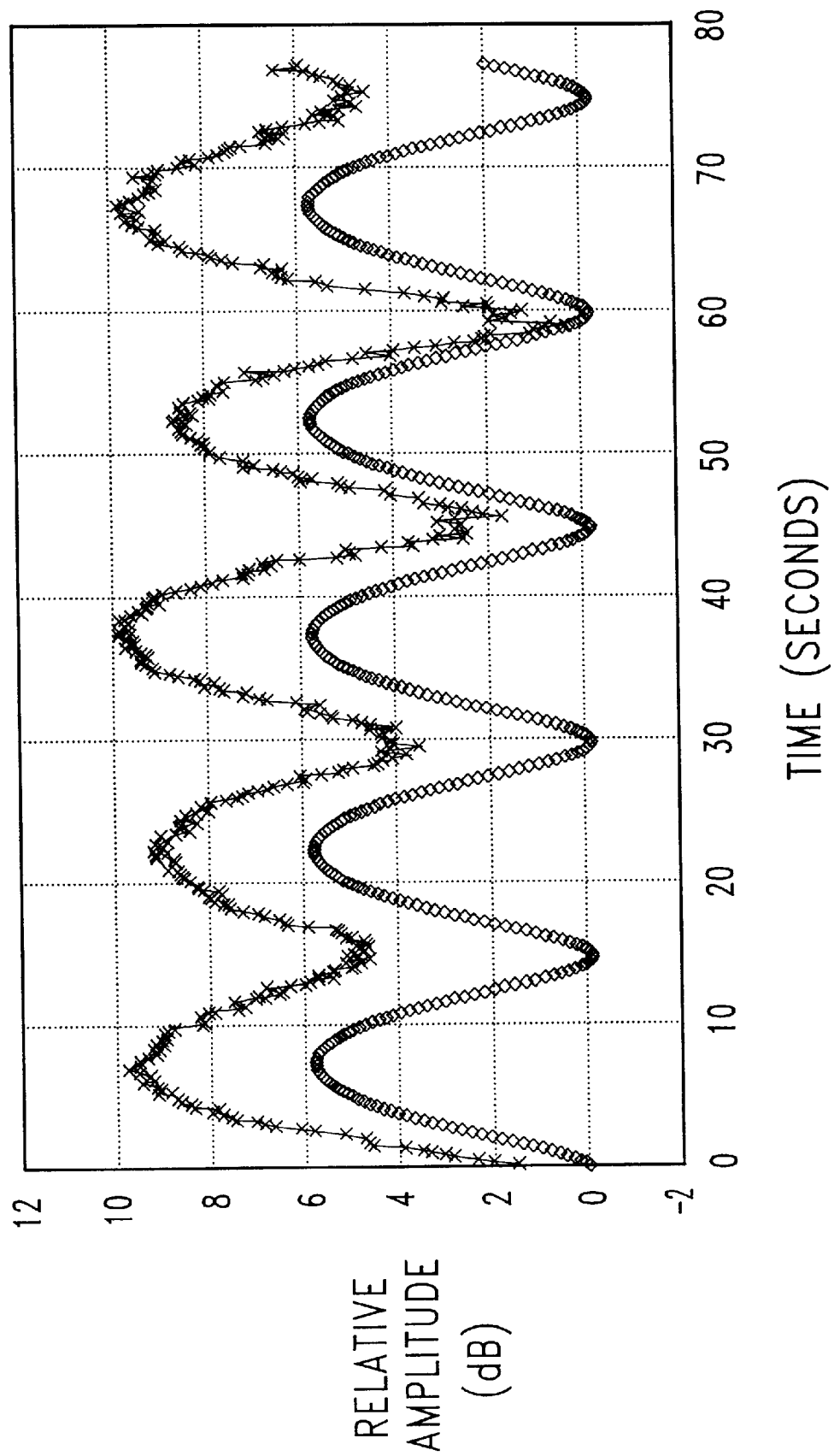
FIG. 22 is a plot of relative amplitude data with fit based on the three parameter model.
Figure 23:
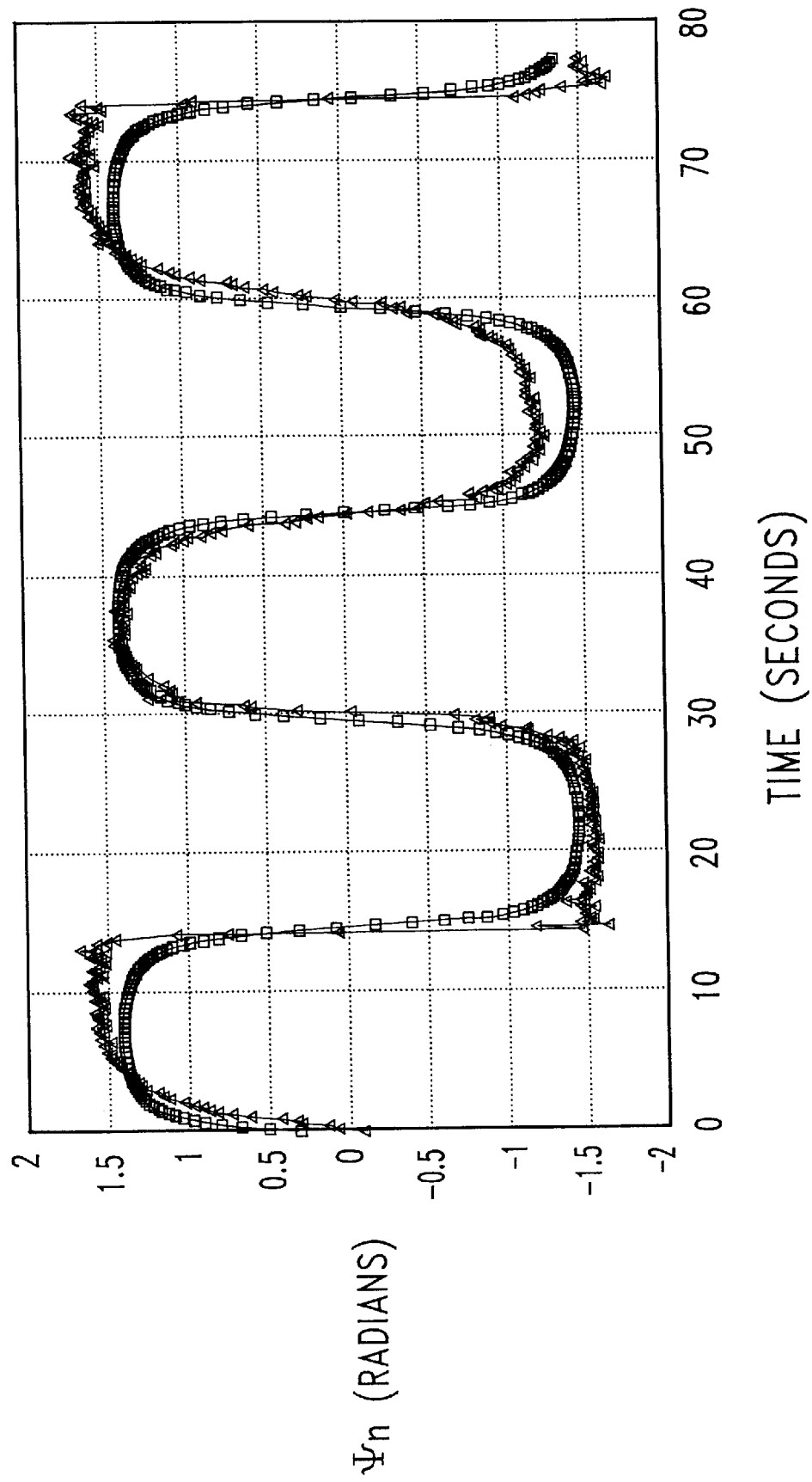
FIG. 23 is a plot of relative phase data with fit based on the three parameter model.

This method gives good results for measurements made on an aluminum shrink-fit specimen with a large EMAT. In this case both the relative amplitude and phase data behaved as predicted by eqn. (34) and (36). However, for the small EMAT, discrepancies occurred such as those shown in FIG. 22, plot of relative amplitude data with fit based on the three parameter model, and FIG. 23, a plot of relative phase data with fir based on the ten parameter model.

For the relative amplitude data the local maxima are not of equal magnitude. This indicates that the attenuation is not the same for waves polarized along the fast and slow directions. The local minima are also of unequal magnitude. This implies that the minima do not repeat when the EMAT rotates by 180°.

Likewise the phase data does not repeat under 180° rotation of the EMAT. This would imply that rotating the EMAT by 180° somehow changes the velocity, which is nonphysical. In addition the rate of change of phase with rotation appears to have asymmetry, another result not in agreement with the 3-parameter model predictions.

Effect of Differential Attenuation: 4-parameter Model

To improve the agreement between model predictions and experiment, we assumed that the attenuation in the fast and slow waves is different. Differential attenuation can be quantified by the parameter $\Delta A_n$: $\Delta A_n = [\exp(-\alpha_f nd) - \exp(-\alpha_s nd)]/2$. If $\Delta A_n > 0$, the attenuation in the slow wave is larger; if $\Delta A_n < 0$ the attenuation in the fast wave is larger.

This model predicts that the local maxima of the relative amplitude still occur for the fast and slow directions, when $\Delta P_n$ is approximately equal to an odd multiple of $\pi$. However if $\Delta A_n > 0$, $A_R$ will be larger for the fast direction and vice versa. This is in qualitative agreement with the data of FIG. 22.

The model also predicts that the local minima will be shifted from $\theta = \pi/4, 3\pi/4$, etc. to $\theta = \pi/4 - \Delta A_n/2, 3\pi/4 + \Delta A_n/2$, etc.. Hence if $\Delta A_n > 0$, the model predicts that maximum interference between the fast and slow wave components no longer occurs with the EMAT oriented midway between the fast and slow directions. Since the slow wave component is smaller, the maximum interference occurs with the EMAT oriented closer to the slow direction by $\Delta A_n/2$ radians.

The 4-parameter model predicts shifts in the zeroes of the additional phase $\Psi_n$ from $\theta = \pi/4, 3\pi/4$, etc. (halfway between slow and fast directions) to $\theta = \pi/4 - \Delta A_n/2, 3\pi/4 + \Delta A_n/2$, etc. The locations of maxima and minima in $\Psi_n$ remain the same as in the 3-parameter fit.

A nonlinear least squares fitting routine was used to implement the 4-parameter model. Since the 4-parameter model can account for the difference in local maxima of $A_R$ it improved the agreement with relative amplitude data. Since it cannot account for differences in measured $\Psi_n$ under 180° rotation it did not significantly improve the fit to phase data.

Inhomogeneity in Velocity and Attenuation—10 Parameter Model

In this case it is assumed that the center of the EMAT aperture is not coincident with the center of rotation. A simple model of EMAT transduction is used to show that the EMAT output voltage is proportional to the particle velocity at the center of the aperture. An instrument is used which measures phase and amplitude of the output voltage. Hence the amplitude and phase data correspond to their values at the aperture center.

Assume that the center of the aperture is offset an amount $r_o$ from the center of rotation, and at an angle $\alpha$ to the EMAT polarization direction. Consider a coordinate system with origin at the center of rotation and axes parallel to the $X_o$- and $Y_o$- directions. In this coordinate system the coordinates of the aperture center are $(r_o \cos(\eta+\alpha), r_o \sin(\eta+\alpha))$.

Assume that the velocities of the slow and fast waves are inhomogeneous. Then for example the slow velocity $V_s$ can be expanded in a (truncated) Taylor series:

$$V_s(r_o \cos\eta, r_o \sin\eta) = V_s(0,0) + (\partial V_s/\partial X_o) r_o \cos(\eta+\alpha) + (\partial V_s/\partial Y_o) r_o \sin(\eta+\alpha). \quad (38)$$

Since $P_s = \omega nd/V_s$, we model the slow phase as follows:

$$P_{s,m} = \gamma_2 + \gamma_5 \cos\eta + \gamma_6 \sin\eta \quad (39)$$

Here $P_{s,m}$ is the measured phase and $\gamma_2$ is the correct phase (phase at the center of rotation). A similar expression can be written for $P_f$:

$$P_{f,m} = \gamma_3 + \gamma_7 \cos\eta + \gamma_8 \sin\eta \quad (40)$$

$\Delta P_n$ is given by $\gamma_2 - \gamma_3$; that is, $\Delta P_n$ is the value of $P_{s,m} - P_{f,m}$ averaged over $0 \leq \eta \leq 2\pi$.

In like fashion we account for inhomogeneity in differential attenuation by rewriting eqn. (30) as $$A^* = (\gamma_4 + \gamma_9 \cos\eta + \gamma_{10} \sin\eta) \cos^2(\eta - \gamma_1), \quad (41)$$

where we use $\theta = \eta - \Phi$, and let $\Phi = \gamma_1$. For example, $\gamma_4$ is the value of $\exp(-(\alpha_s - \alpha_f)nd)$ at the center of rotation. The same procedure which leads to eqn. (41) also gives $B^* = \sin^2(\eta - \gamma_1)$.

From the above we see that this model requires a total of 10 parameters (6 for phase; 3 for attenuation; 1 for $\Phi$).

Figure 24:
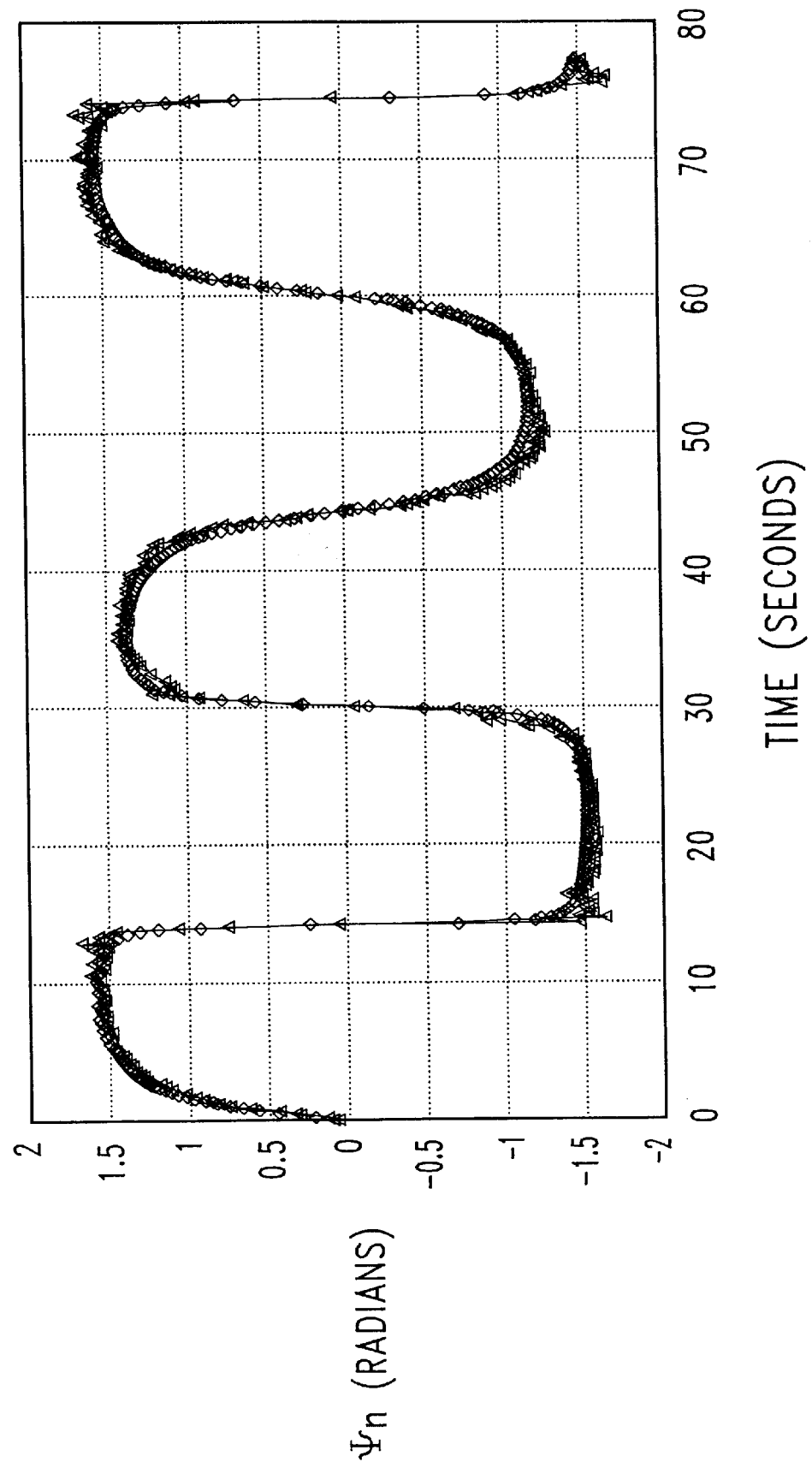
FIG. 24 is a plot of relative phase data with fit based on the ten parameter model.

Improved agreement was found between model predictions and the phase data; see FIG. 24, relative phase data with fit based on ten parameter model. The agreement between predicted and measured relative amplitude also improved, but to a lesser degree.

Effect of Varying Transducer Gain With Rotation: 13-parameter Model

In this model we kept the same functional forms for $A^*$, $B^*$, and the phase $\Psi_n$. However we now assumed that the amplitude is given by $$a(\theta; \Delta P_n) = \{f(\eta)[A^{*2} + B^{*2} + 2A^*B^*\cos(P_s - P_f)]\}^{1/2} \quad (42)$$

where $$f(\eta) = \gamma_{11} + \gamma_{12} \cos\eta + \gamma_{13} \sin\eta. \quad (43)$$

The term $f(\eta)$ allows for variation in apparent transducer gain as the EMAT rotates.

Figure 25:
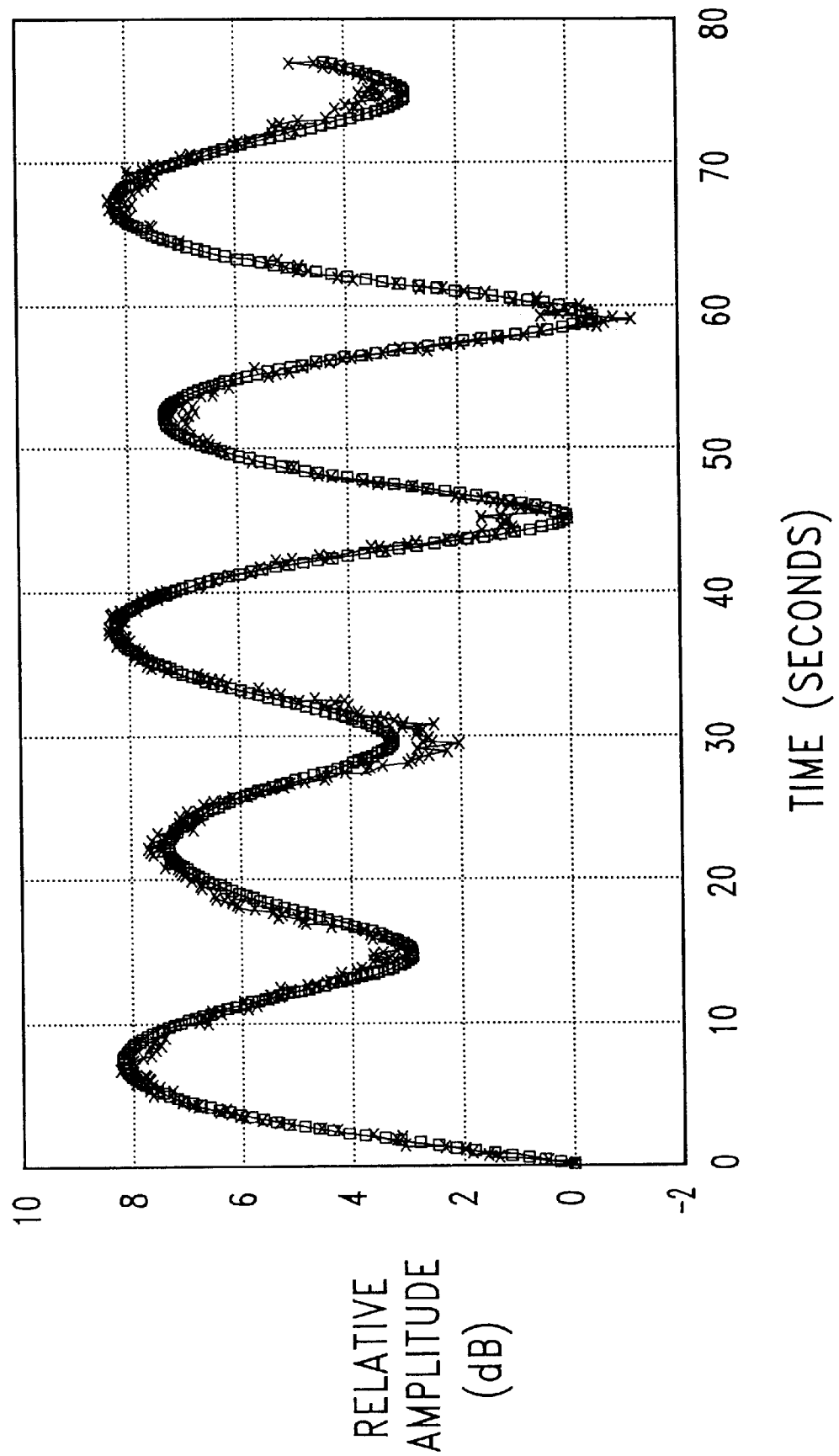
FIG. 25 is a plot of relative amplitude data with fit based on the thirteen parameter model.

The predicted phase, based on 13-parameter model, is now almost indistinguishable from the phase data. There was also improvement in the fit to the amplitude data using this model; see FIG. 25, a plot of relative amplitude data with fit based on thirteen parameter model.

The relation between the stress changes and changes in (weighted) TOF is given by:

$$\Delta\sigma_{xx} = K_{11}\Delta\tau_1 + K_{12}\Delta\tau_2$$

$$\Delta\sigma_{yy} = K_{21}\Delta\tau_1 + K_{22}\Delta\tau_2 \quad (44)$$

$$\Delta\sigma_{xy} = K_{33}\Delta\tau_3$$

Here we define:

$$\tau_1 = (T_s \cos^2\Phi + T_f \sin^2\Phi)/T_o;$$

$$\tau_2 = (T_f \cos^2\Phi + T_s \sin^2\Phi)/T_o; \quad (45)$$

$$\tau_3 = [(T_s - T_f)\sin^2 2\Phi]/2T_o.$$

$\Phi$ is the angle between the pure-mode directions ("acoustic axes") in the unstressed and stressed states (see FIG. 2). $T_s$ is the TOF of the wave polarized along the "slow" direction (X-axis) and $T_f$ is the corresponding TOF in the "fast" direction (Y-axis). $T_o$ is the average TOF.

Effect of Birefringence on Time-of-Flight

Consider the case of an SH-wave generated when the EMAT is oriented at an arbitrary angle $\eta$ to the transverse direction; see FIG. 5. The wave will also be at an angle $\theta$ to the new "slow" polarization direction (X-axis), which is itself at an angle $\phi$ to the transverse direction. Hence $\theta = \eta - \phi$.

The wave will split into components polarized along the X-Y axes, with amplitudes proportional to $\cos\theta$, $\sin\theta$ respectively. The components propagate with different phase velocities. The faster component, polarized along the Y-axis, has velocity $V_f$; the component polarized along the X-axis has velocity $V_s$.

The particle velocity in the received wave is just the projection of these components along the EMAT polarization direction. Normalizing by the amplitude $A_o$ generated directly under the EMAT, we have for the particle velocity $A_n$ in the $n_{th}$ echo;

$$(A_n/A_o) = \cos^2\theta \sin(\omega(t - 2nd/V_s)) + \sin^2\theta \sin(\omega(t - 2nd/V_f)) \quad (46)$$

Here we assume toneburst operation with center frequency $\omega$, and let $d$=plate thickness. For simplicity we have ignored the effect of attenuation.

Using the definition of birefringence we can rewrite the above as $$(A_n/A_o) = \cos^2\theta \sin(\omega(t - t_o - t_o B/2)) + \sin^2\theta \sin(\theta(t - t_o + t_o B/2)) \quad (47)$$

Here $t_o$ is the average transit time in the $n_{th}$ echo, in the absence of texture and stress: $t_o = 2nd/V_o$. Note the advance in phase in the slow wave of amount $\omega t_o B/2$, and phase retardation of $-\omega t_o B/2$ in the fast wave. Also note that the difference in phase $\Delta P$ between the fast and slow wave components is: $\Delta P = \omega t_o B$.

Figure 15:
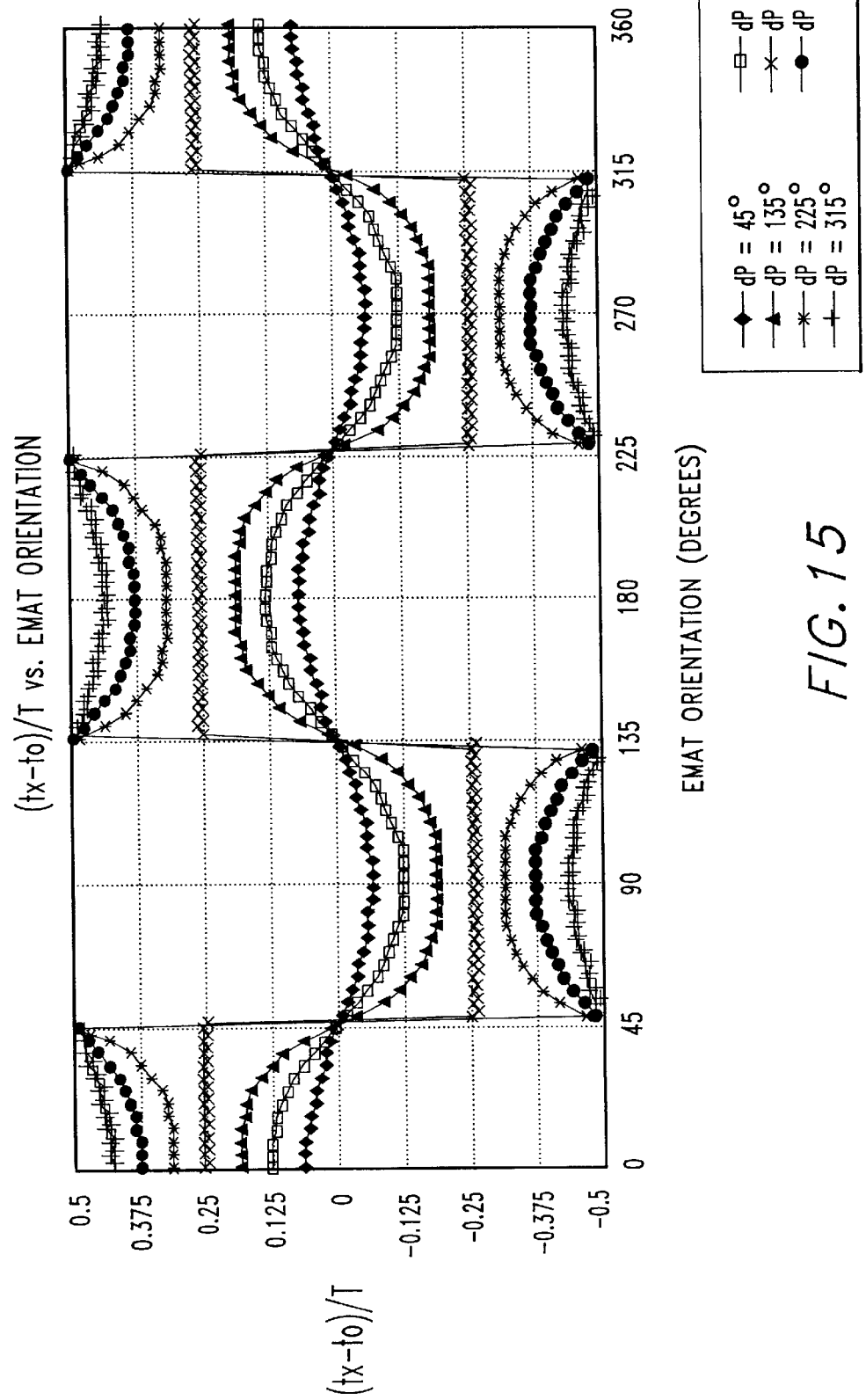
FIG. 15 is a plot of $(t_x-t_o)/T$ as a function of θ, following the same cycle in waveform.

The apparent time-of-flight of the wave as a function of EMAT angle. Ideally this measurement is done by tracking the same zero-crossing of a selected cycle in the toneburst, as the EMAT rotates. This process can be simulated by calculating the change in zero-crossing time $t_x$ (where the amplitude =0) from eqn. (4). The results are shown in FIG. 15 where we plot $(t_x - t_o)/T$ as a function of $\theta$, for different values of $\Delta P$. Here T is the period of the toneburst center frequency.

Note that $t_x - t_o$ behaves sinusoidally (as a function of $\theta$) for small values of $\Delta P$. It has a local maximum when $\theta = 0°$, and a local minimum when $\theta = 90°$. When $\Delta P$ is 180°, $t_x - t_o$ behaves like a square wave with peak-to-peak amplitude of ½ period. When $\Delta P$ exceeds 180° the function is discontinuous, having a jump of one period at $\theta = 45°, 135°$, etc. Now the zero-crossing time has a local minimum at $\theta = 0°$ (the slow direction), and a local maximum at $\theta = 90°$ (the fast direction).

We can explain the behavior of $t_x - t_o$ by using a phasor representation. We rewrite, for example, $\sin(\omega(t - t_o - t_o B/2)) = \text{Im}(\exp(j(\omega(t-t_o) - \Delta P/2))$ and use trigonometric identities to put eqn. (4) in the form:

$$(A_n/A_o) = \{a(\theta; \Delta P) \exp(-j\psi(\theta; \Delta P))\}\exp(j(\omega(t - t_o)) \quad (48)$$

The term in braces is a phasor with amplitude a $(\theta;\Delta P)$ and phase angle $\psi(\theta;\Delta P)$.

The amplitude a $(\theta;\Delta P)$ is given by:

$$a(\theta;\Delta P)=\{1-\sin^2\theta\sin^2(\Delta P/2)\}^{1/2}. \qquad (49)$$

Hence a $(\theta;\Delta P)$ is modulated due to interference between the fast and slow wave components. It is a maximum when the transducer is oriented along the fast and slow directions. It is a minimum with the transducer oriented halfway between these directions; when $\Delta P=180°$ and $\theta=45°$, $135°$, etc the amplitude vanishes. The interference also causes an additional phase shift, given by $\psi(\theta;\Delta P)$:

$$\psi(\theta;\Delta P)=\tan^{-1}\{\tan(\Delta P/2)\cos 2\theta\}. \qquad (50)$$

From eqn. (48), zero crossings occur when the phase equals an integer multiple of $\pi$. This correspond to times $t=t_x$, where $$\omega(t_x-t_o)-\psi(\theta;\Delta P)=2n\pi. \qquad (51)$$

with n=0,1, . . . etc. Hence the behavior of $t_x-t_o$ is directly related to that of $\omega(\theta;\Delta P)$. For example, there are local extrema in $t_x-t_o$ when $d\omega/d\theta=0$; these occur at $\theta=0°$ and $90°$.

Figure 17:
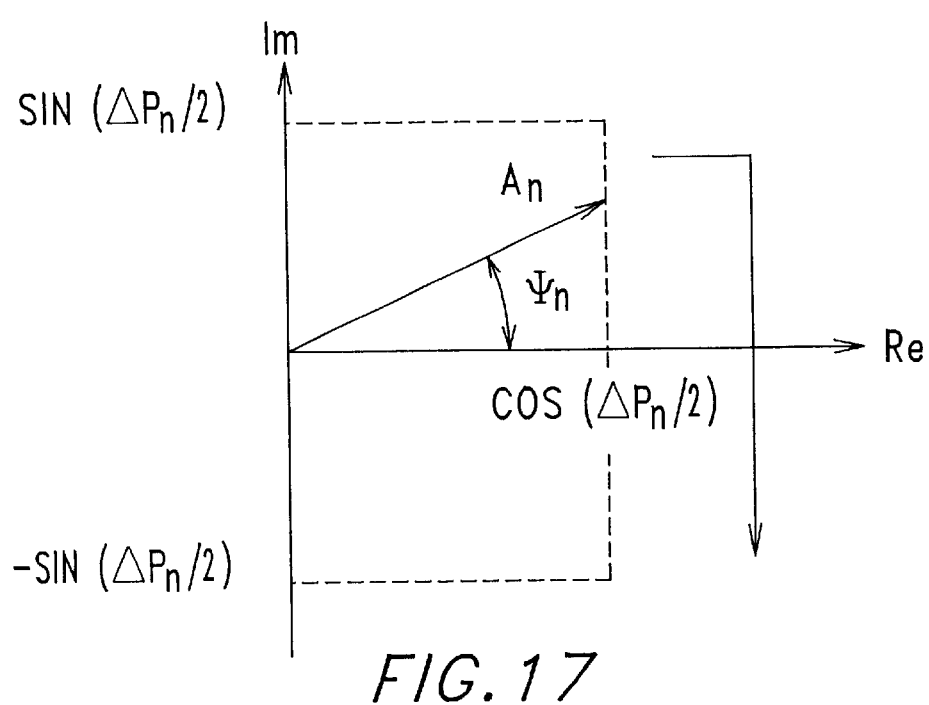
FIG. 17 is a plot of the behavior of the phasor a(θ;ΔP) exp(−jψ(θ;ΔP)) in the complex plane as θ varies from 0° (the slow direction) to 90° (the fast direction).

FIG. 17 shows the behavior of the phasor a $(\theta;\Delta P)$ $\exp(-j\psi(\theta;\Delta P))$ in the complex plane as $\theta$ varies from 0° (the slow direction) to 90° (the fast direction). Consider first the case of $\Delta P<180°$. From eqn. (48), the tip of the phasor lies on the unit circle when $\theta=0°$ and $90°$. As $\theta$ increases from 0° to 45°, the tip tracks along a line parallel to the imaginary axis in the first quadrant. At $\theta=45°$, the tip is on the real axis, at distance cos $\Delta P/2$ from the origin. For $45°<\theta<90°$, the tip lies in the fourth quadrant. Hence $\psi$ and $t_x$-to vary continuously as the transducer rotates from the slow to the fast directions.

Figure 16:
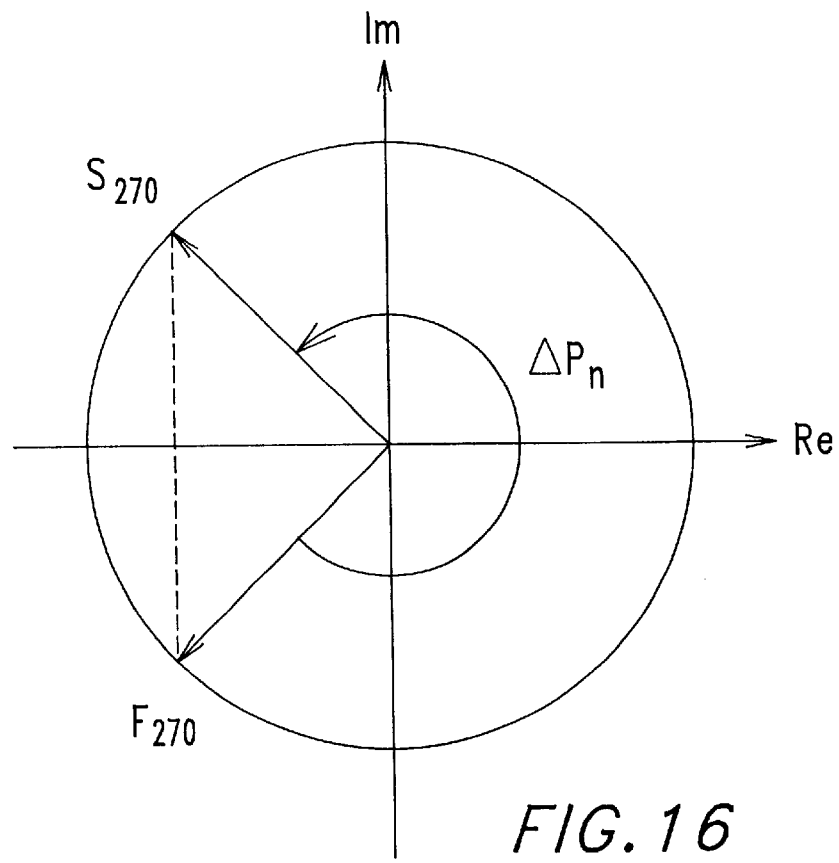
FIG. 16 is a plot of ΔP>0.

FIG. 16 illustrates the situation when $\Delta P >180°$. Here we show how the phasor tracks for $\Delta P=270°$. For $\theta=0°$ (slow direction) the tip is at the location labeled "$S_{270}$", which is in the second quadrant. The tip reaches the negative real axis for $\theta=45°$. This axis is a branch cut in the complex plane for the arctangent function. Consequently the phasor jumps to another sheet; this gives a jump of $2\pi$ in phase. (Likewise, $t_x-t_o$ has a jump of one period at this angle.) The phasor then tracks in the third quadrant, in the new sheet, reaching the location labeled "$F_{270}$" for $\theta=90°$ (fast direction).

The analysis assumes that the TOF of the same zero crossing is measured. However, as mentioned previously, the method of TOF measurement used by our system can result in "cycle skipping".

We illustrate the phenomenon of cycle skipping by the following example. Assume $\Delta P$ is slightly greater than 180°. Then from FIG. 15 we see that $t_x-t_o$ increases from approximately T/4 at the slow direction to T/2 at $\theta=45°$. (Here T=one period of the toneburst). There it experiences a decrease of one period, and then increases to a local maximum of about −T/4 at the fast direction. It then decreases to −T/2 at $\theta=135°$, where it has a jump of a period, becoming T/2. Finally, $t_x$-to decreases to its starting value of T/4 at $\theta=180°$.

The EMAT is oriented along the $X_o$ axis at the measurement location and the gate is centered on 2 peaks in the middle of the toneburst. In general the $X_o$ axis does not coincide with $\theta=0°$ (the slow direction in the stressed state).

For purposes of illustration, the EMAT starts rotating from $\theta=22.5°$. The gate is centered on 2 peaks in the middle of the toneburst. We assume the gate width is slightly less than 2 periods. Then the first peak is located at about ½ period from the leading edge of the gate when the EMAT begins rotating.

As the EMAT rotates from $\theta=22.5°$ to $45°$, $t_x-t_o$ increases by about T/4. Hence the first peak moves back in time so that it is located at about (¾)T from the leading edge of the gate. At $\theta=45°$, the TOF decreases by T so that this peak now moves outside the gate; the second peak is now at about (¾)T from the leading edge. The TOF measurement system therefore "locks on" to the zero crossing following the second peak, at $\theta=45°$.

Therefore the TOF measurement does not show any discontinuity at $\theta=45°$. This is illustrated by the open circles in FIG. 18, a plot of measured TOF. These data represent values of $t_x-t_o$ for the zero crossing following the second peak.

Figure 18:
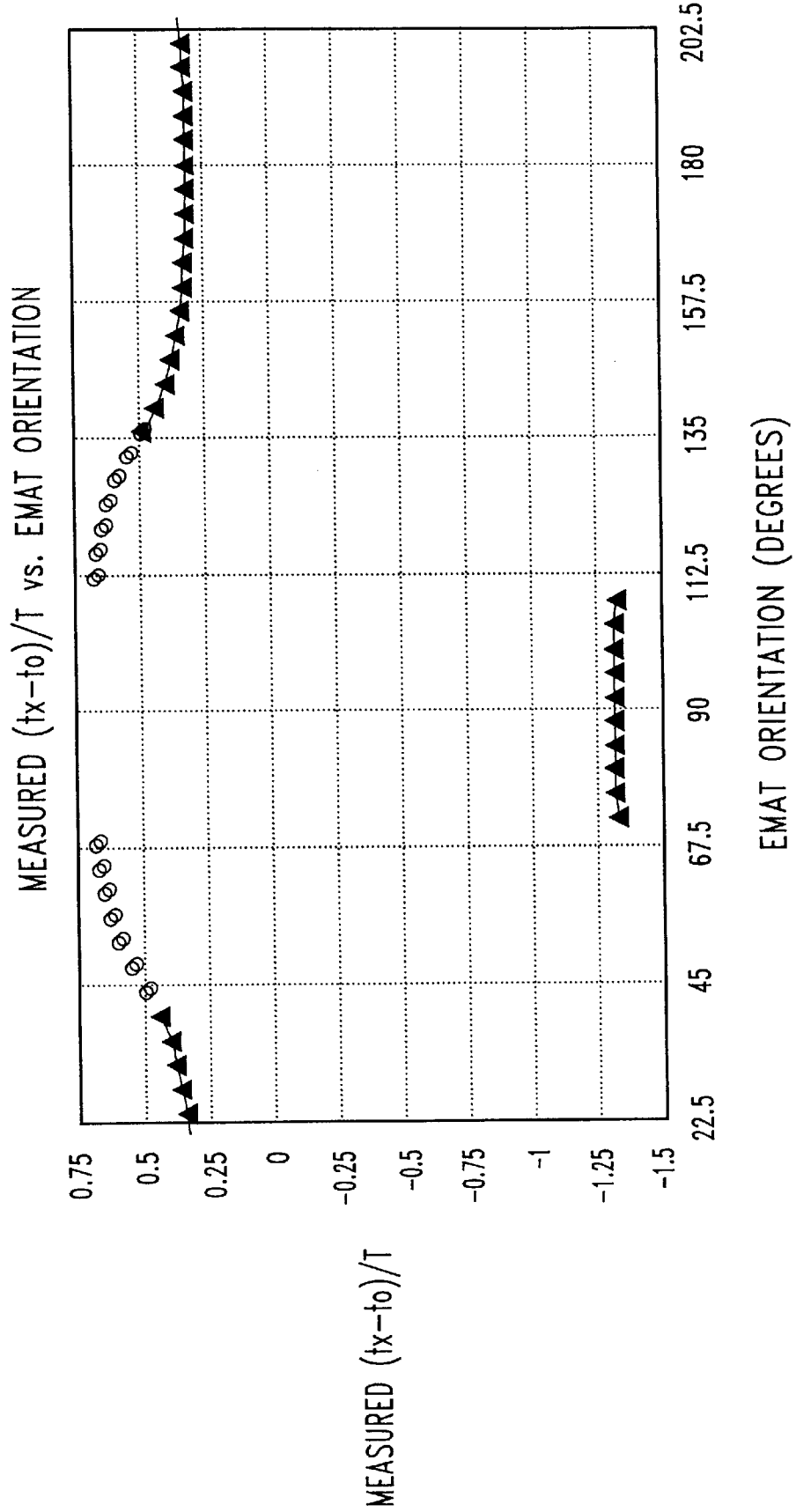
FIG. 18 is a plot of measured TOF, with fixed gate.

As $\theta$ approaches 90°, the TOF increases by about T/4; the first peak moves later in time. Eventually it crosses the leading edge of the gate; at this orientation the system locks on to the zero crossing following the first peak. This results in a discontinuity in measured TOF of a period, as shown in FIG. 18.

Now $t_x-t_o$ has a local maximum at $\theta=90°$ so the TOF begins to decrease again. The first peak, which had been slightly inside the gate, now moves outside the leading edge; the measured TOF again jumps by one period. The TOF data measured by the instrument then follows the values of $t_x-t_o$ for the zero crossing following the second peak until $\theta=135°$.

There is another increase of T in $t_x-t_o$ at this angle, so the first peak moves back inside the gate with another jump of T in the measurement of TOF. The system then tracks the TOF of the zero crossing following the first peak. The corresponding TOF data is shown in FIG. 18, terminating at 202.5°. There the EMAT has rotated 180° from its initial value of 22.5°. Since $t_x-t_o$ repeats under 180° rotation, there is no need to continue the analysis further.

Algorithm for Determination of Orientation of
Pure-Mode Polarization Directions of TOF Data The digital TOF instrument records the zero-crossing times of a selected cycle in the toneburst as the EMAT rotates. (This process is described in detail later). We start the rotation counterclockwise from the $X_o$-axis (slow direction in the absence of stress). Hence the instrument records a TOF as function of the angle $\eta$; see FIG. 5. The algorithm first calculates the average arrival time $t_o$. This is subtracted from all the $t_x$ and a pseudo-phase P* is calculated:

$$P^*=\omega(t_x-t_o). \qquad (52)$$

(Note that by setting n=0 in eqn. (53) we have $P^*=\psi$.) For $\Delta P >180°$ $t_x$ jumps by a period at $\theta=45°$, $135°$,etc.; see FIG. 16. Consequently the value of the pseudo-phase P* can be greater than $\pi$. We want to deal only with values in the range $(-\pi/2, \pi/2)$. To do this algorithm next calculates P'=tan P*, and then calculates P#=arctan (P'). This process maps P* into P#; the latter is now bounded so that $-\pi/2<P\#<\pi/2$. We have forced all P# to lie within the bounds of the principal value of the arctangent function. This allows us to determine angle $\Phi$ by the following procedure. The algorithm calculates a "synthetic phase"

$$\psi^{syn}(\theta;\Delta P)=\tan^{-1}\{\tan(\Delta P/2)\cos 2(\eta-\Phi^*)\} \qquad (53)$$

where $\Phi^*$ is an assumed value for $\Phi$. (Recall that $\theta=\eta-\Phi$; see FIG. 5) The value of $\Delta P$ is determined from the difference of the maximum and minimum value of P#.

The values of $\psi^{syn}(\theta;\Delta P)$ are calculated for all $\eta$ for each assumed $\Phi^*$ in the range $(0, \pi)$. For each value of $\Phi^*$ the algorithm calculates the residual:

$$R(\Phi^*) = \Sigma[P\#(\eta_i) - \psi^{syn}(\eta_i, \Phi^*)]^2 \quad (54)$$

Figure 19:
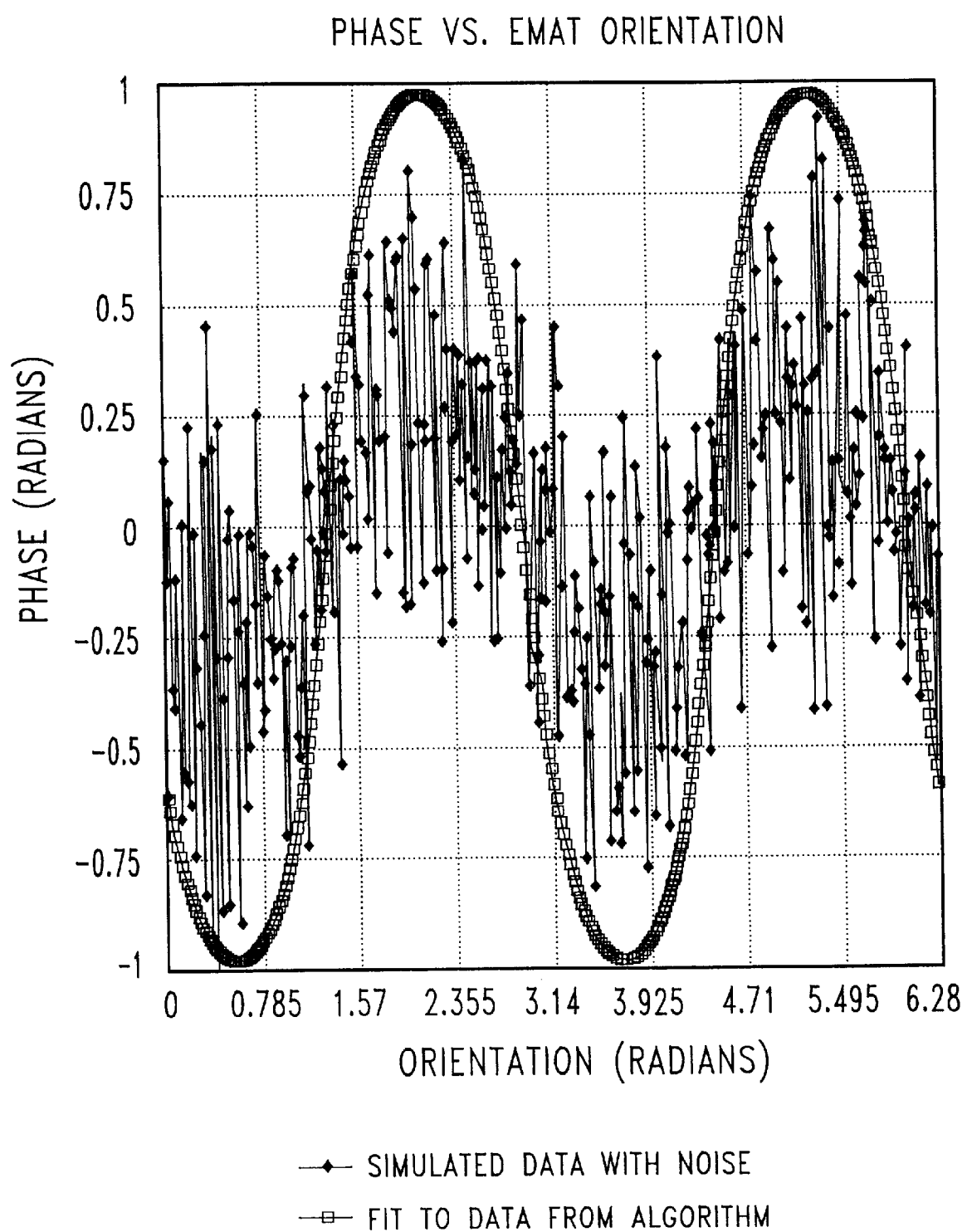
FIG. 19 relates the ability of algorithm to correctly determine PMPD in the presence of noise.

It then identifies the value of $\Phi^*$ which gives the minimum residual; this is the best estimate of $\Phi$. The algorithm is tolerant of errors introduced by noise in TOF measurement. This is illustrated by FIG. 19, which relates the ability of algorithm to correctly determine PMPD in the presence of noise. There we calculated $\psi$ for the case of $\Phi=60°$, $\Delta P=180°$ and frequency=2 MHz; the maximum difference in TOF is therefore 125 ns. Then we superposed random noise with peak amplitude of 100 ns. The solid curve represents the best fit to the data from our algorithm, which for this case predicted a value of $\Phi=61°$.

Modifications of the Basic Algorithm to Compensate for Artifacts in TOF Data

A fixed gate location is set (prior to rotating the EMAT) so that there are two peaks located symmetrically in the gate. That is, one peak is approximately centered in the first (earliest in time) half of the gate, and the other peak centered in the second half. The instrument is designed to detect the first zero-crossing following the peak in the first half of the gate.

Because of the additional phase $\psi$ introduced by birefringence, peaks can migrate into and out of the gate as the EMAT rotates. This is especially true for those echoes for which $\Delta P > 180°$, since $t_x$ has a discontinuity of a period at $\theta=45°$, 135°, etc.

In principle as one peak moves out of the gate, another should almost immediately replace it. Hence the instrument will no longer measure the TOF of the same zero crossing; it will jump from one cycle to the next.

However, this poses no problem the our algorithm to determine the orientation of the pure-mode polarization directions from the TOF data taken under rotation. The algorithm automatically compensates for discontinuities of one (or more) periods when it maps the pseudo-phase data P* into P#, which is bounded by the principal values of the arctangent function.

Problems can arise, however if the signal amplitude falls below a certain threshold. The instrument then generates an "error flag" by inserting an apparent TOF of 50.000 μs in the data file.

In principle this can be avoided by not gating any echo having fast and slow wave components out of phase by approximately 180°, 540°, etc. However this is inconvenient since it requires the operator to first rotate the EMAT, observe the echo pattern, and note which echoes are partially extinguished. Then the operator would set the gate location (on an echo that is not extinguished) and repeat the rotation, this time collecting the TOF data.

To avoid this unnecessary labor, the algorithm searches through the TOF data for values of 50.000 μs. If it finds one of these artifacts, the algorithm replaces the artifact with the (good) TOF data taken at the immediately preceding EMAT angle. In this way it "splices" the artifact data to the (good) data to avoid discontinuities. We have found that even if there are multiple artifacts (which will give a "plateau" region), the algorithm is robust enough to determine $\Phi$ to within about 1° of the correct value.

There is another reason for using this "splicing" procedure. Recall that when we calculate the pseudo-phase P*, we use the value of the average TOF, $t_o$. If there are multiple artifacts where the instrument artificially sets arrival time values to 50.000 μs, the algorithm will not calculate the correct average TOF. Consequently some values of P# may not fall inside the range $(-\pi/2, \pi/2)$. The algorithm will then be trying to fit the synthetic data $\psi$ to a distorted data set of P#. This may otherwise cause errors in the prediction of $\Phi$.

Determination of Stresses From TOF Data

Referring again to equ. (44) and (45), the K's are acoustoelastic constants determined by performing uniaxial tension tests with specimens cut at different angles to the specimen rolling direction. For example:

$$K_{11} = (d\tau_1/d\sigma_{xx})^{-1}, K_{12} = (d\tau_2/d\sigma_{xx})^{-1}$$

for a uniaxial specimen cut along the transverse direction.

Once the K's are known (either from values in the literature or by performing the uniaxial tension tests described above), the procedure to determine stress changes proceeds as follows.

The transducer is placed at selected measurement locations on the specimen in the initial state. TOFs and $\Phi$ are then measured (note: if the initial state is unstressed, then $\Phi$ is zero and it is only necessary to measure TOFs). The specimen is then stressed; at some convenient time later the EMAT is repositioned at the same locations and a new set of TOFs and $\Phi$ measured. Values of τ's are calculated (see eqn. (45)) for both stressed and unstressed state, and stress changes calculated from eqn. (44).

Since the K's are large, small errors in TOF's result in large stress errors. Conversely, stress causes only small changes in TOF's. An error analysis shows that to resolve 10 MPa of stress in steel requires resolution in TOF of order of 10 ppm.

The transduction mechanism of the EMAT makes it ideal for this application. Conventional piezoelectric transducers require couplants to transmit sound from transducer to specimen. It is difficult (but not impossible) to accurately control the couplant thickness, but special fixturing is required. In contrast, EMATs generate sound directly in the surface of the specimen and can work with clearances of a few mm. Hence they can be rapidly scanned and rotated to collect the required data.

Figure 3:
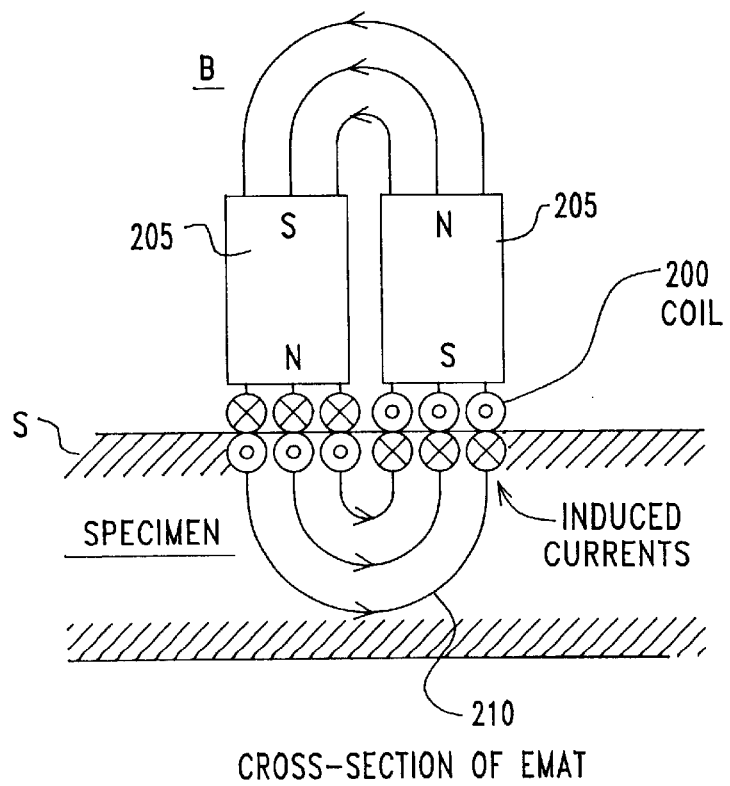
FIG. 3 shows a cross-section of the rotating EMAT.

FIG. 3 shows a cross-section of the rotating EMAT. It consists of a "racetrack" coil 200, excited by a high-power toneburst by the commercial instrument. Magnets 205 (with opposite polarity) are placed above the "straight" sides of the coil. The reaction force $F_L$ between the magnetic induction B with the induced eddy current 210 density J is: $F_L = J \times B$. This causes a shearing force at the specimen S surface, which sets up a propagating SH wave.

Figure 4:
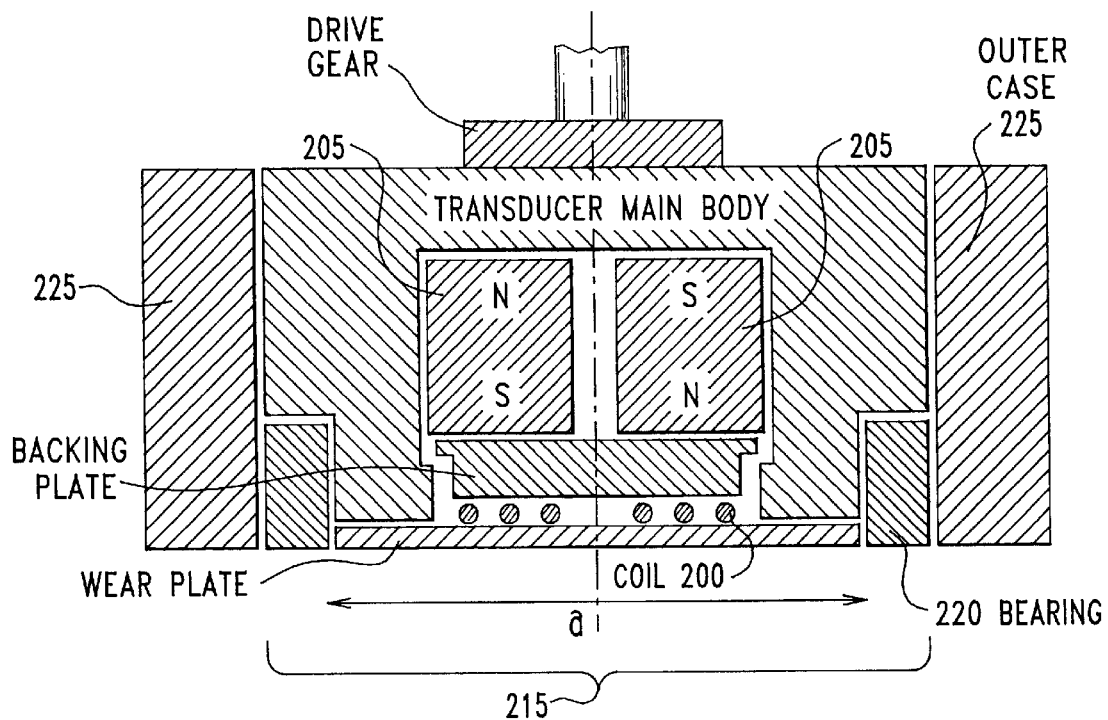
FIG. 4 shows the implementation of the motorized, rotating EMAT.

FIG. 4 shows the implementation of the motorized, rotating EMAT. The coil 200 and magnet 205 are contained inside a rotating cylinder 215. The bearings 220 are press-fit onto the cylinder 215 and are seated inside the (fixed) outer case 225. The motor (see FIG. 14) is mounted on the case and rotates the cylinder by means of a gear train or chain drive. Offsetting the motor in this manner allows rotation of the EMAT without twisting the cable (not shown) which connects the EMAT to the commercial instrument. The specifications of the preferred embodiment include an effective EMAT aperture, a, of 25 ×25 mm and an angular velocity of 1 rpm.

The EMAT is used to generate and receive waves which are used to determine $\Phi$ (in conjunction with the phase-sensitive commercial instrument), and to generate and receive waves polarized along the pure-mode directions to determine the TOF's in eqn. (45).

FIG. 5 shows the EMAT generating a wave polarized at angle Θ to the acoustic axes in the stressed configuration.

The EMAT is polarized at a known angle η to the $X_o$-axis (the transverse direction). The SH wave generated by the toneburst from the EMAT splits into components polarized along the X,Y axes, having amplitude cos θ, sin θ, respectively. Each wave component propagates with a characteristic velocity. Upon recombining the components along the transducer polarization direction, we find that the particle velocity U is given by:

$$U^2 \sim \exp(j P_{ave})\{\cos^2\theta \exp(j \Delta P) + \sin^2\theta \exp(-j \Delta P)\} \quad (55)$$

Here $P_{ave}$ is the average phase and $\Delta P = P_s - P_f$ is difference in phase between SH wave components polarized along the slow and fast directions. The term in braces represents the effect of interference between these components. It is this term that we use to determine Φ.

Algebraic manipulation allows this term to be rewritten in the form $a(\theta) \exp(j\psi(\theta))$ where $\psi(\theta)$ is the additional phase resulting from interference. $\psi(\eta)$ is determined from measurements made with the phase-sensitive commercial instrument as the EMAT is rotated. We then calculate:

$$\psi(\theta) = \arctan\{\tan^{-1}(\Delta P/2) \cos 2\theta\} \quad (56)$$

Figure 6:
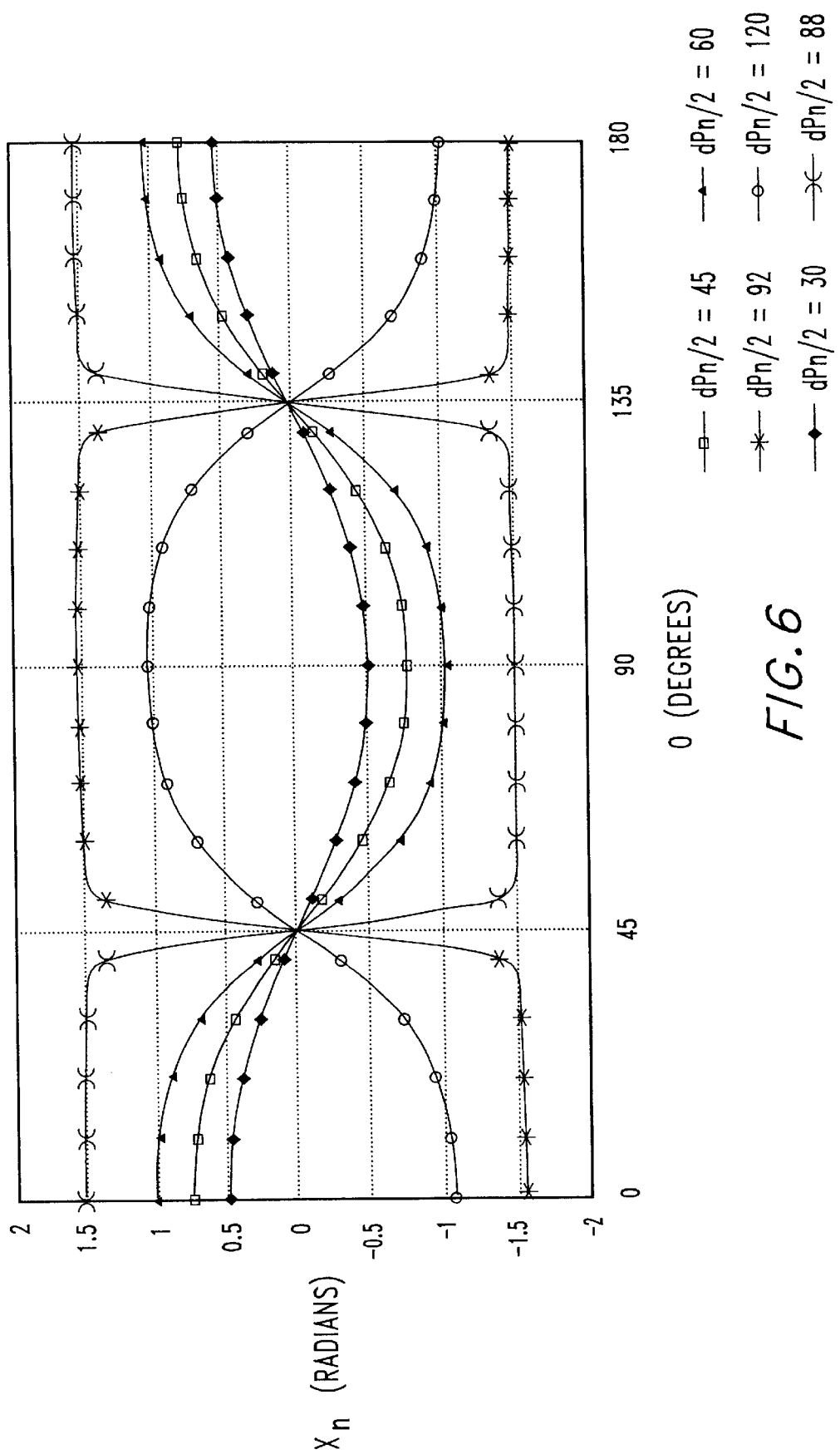
FIG. 6 shows behavior of additional phase for different values of the parameter ΔP.

FIG. 6 behavior of additional phase for different values of the parameter ΔP. (see FIG. 5) θ=η−Φ and Φ are unknown.

X(η) is measured with the phase sensitive instrument as the EMAT is rotated. Software supplied with the instrument generates a file containing "clock time" and phase. Clock time is recorded as time since the EMAT is polarized along the transverse axis ($X_o$-axis in FIG. 5). The file is recorded on the computer hard disk for further evaluation by our algorithm. The operator imports the data from the file and runs the algorithm.

In the first step, clock time is converted to angle η by: η=ωt where ω is the angular velocity of the rotating EMAT. The algorithm next determines the maximum and minimum phase $\psi_{max}$ and $\psi_{min}$. The difference in phase ΔP is calculated from: $\Delta P = \psi_{max} - \psi_{min}$. From values of η and ΔP, the "synthetic phase" is calculated:

$$\psi_{syn}(\eta;\Phi^*) = \arctan\{\tan^{-1}(\Delta P/2) \cos 2(\eta - \Phi^*)\} \quad (57)$$

θ=η−Φ; here Φ* is the assumed value of Φ. For each value of Φ* (in 1° increments) in the interval between e of 0 and 180 degrees, the algorithm calculates the residual $$R(\Phi^*) = \Sigma(\psi_{syn}(\eta_i;\Phi^*) - \psi(\eta_i;\Phi^*)). \quad (58)$$

Here $\eta_I = \omega t_I$ where $t_I$ is the $I_{th}$ increment of clock time. The algorithm searches through values of R(Φ*) to find the minimum. The corresponding value of Φ* gives the best estimate of Φ.

Figure 7:
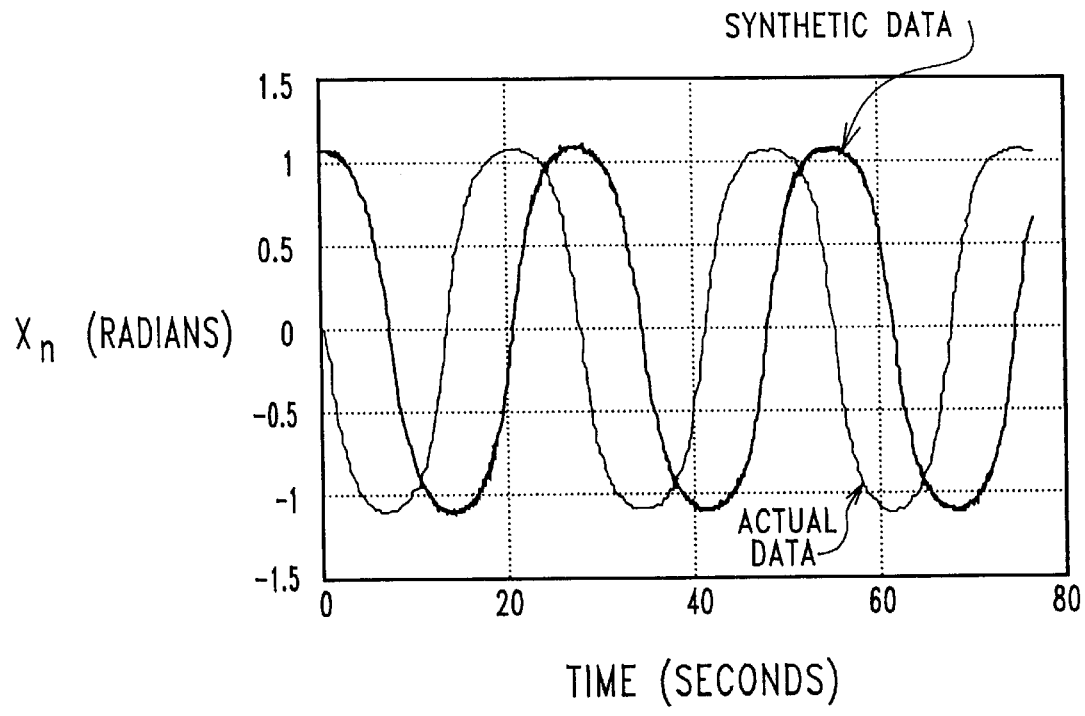
FIG. 7 depicts the case where φ*=0(the correct value of Φ is 46°).
Figure 8:
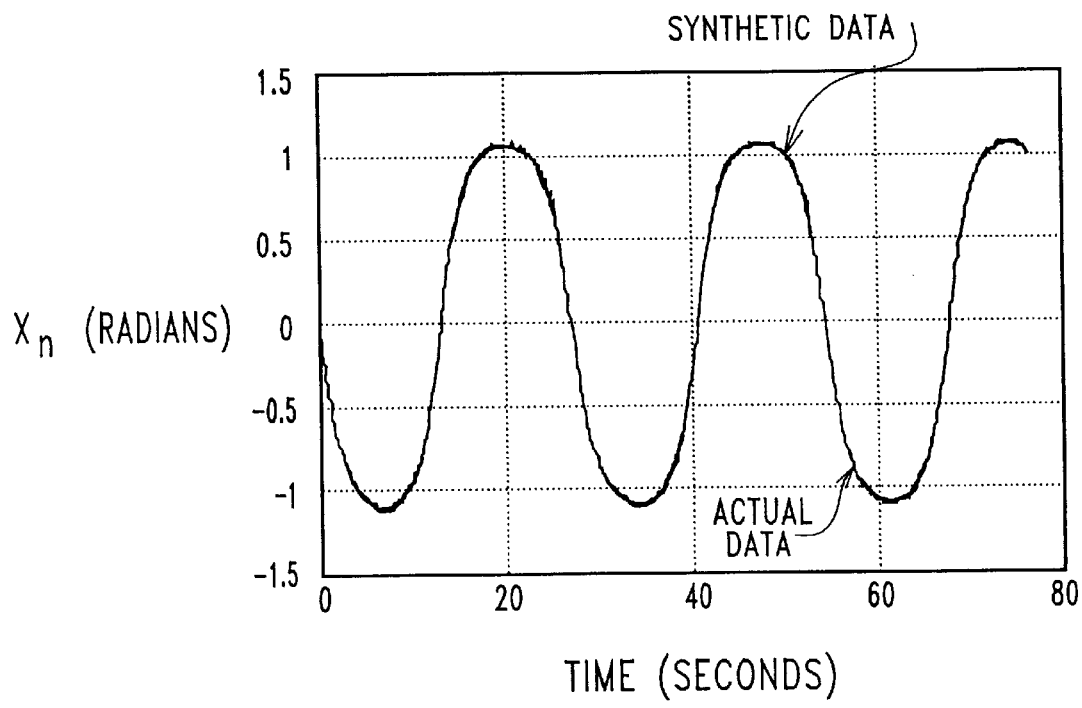
FIG. 8 shows real and synthetic data after the algorithm determines Φ=46°.

To illustrate the procedure, FIG. 7 depicts a chart where the data are taken at locations where the correct value of Φ is 46°, with the synthetic data calculated for Φ*=0°. FIG. 8 shows real and synthetic data after the algorithm determines Φ=46°. Note the good agreement between the two.

The EMAT is typically rotated and phase data is recorded for about 80 seconds with the 1 rpm motor. Once Φ is determined, the EMAT is rotated with the motor or by hand so that it is polarized along, for example, the X-axis (see FIG. 5). The TOF of the wave polarized along this axis is measured with our digital gate/counter system, described next.

The operator selects a particular cycle on a particular echo for measurement purposes. These must be the same for measurements taken in the unstressed and stressed states. This is done by manually adjusting the location (in time) of the digital gate 135 such that it is in the ON state just before the zero crossing. Then a comparator circuit generates a square pulse when the zero crossing occurs. This pulse is input to the STOP channel of the counter 100 (see FIG. 1). The counter 100 is started by a trigger pulse from the commercial ultrasonic instrument 115. This pulse is coincident with the toneburst, RF pulse out, that drives the EMAT.

Figure 9:
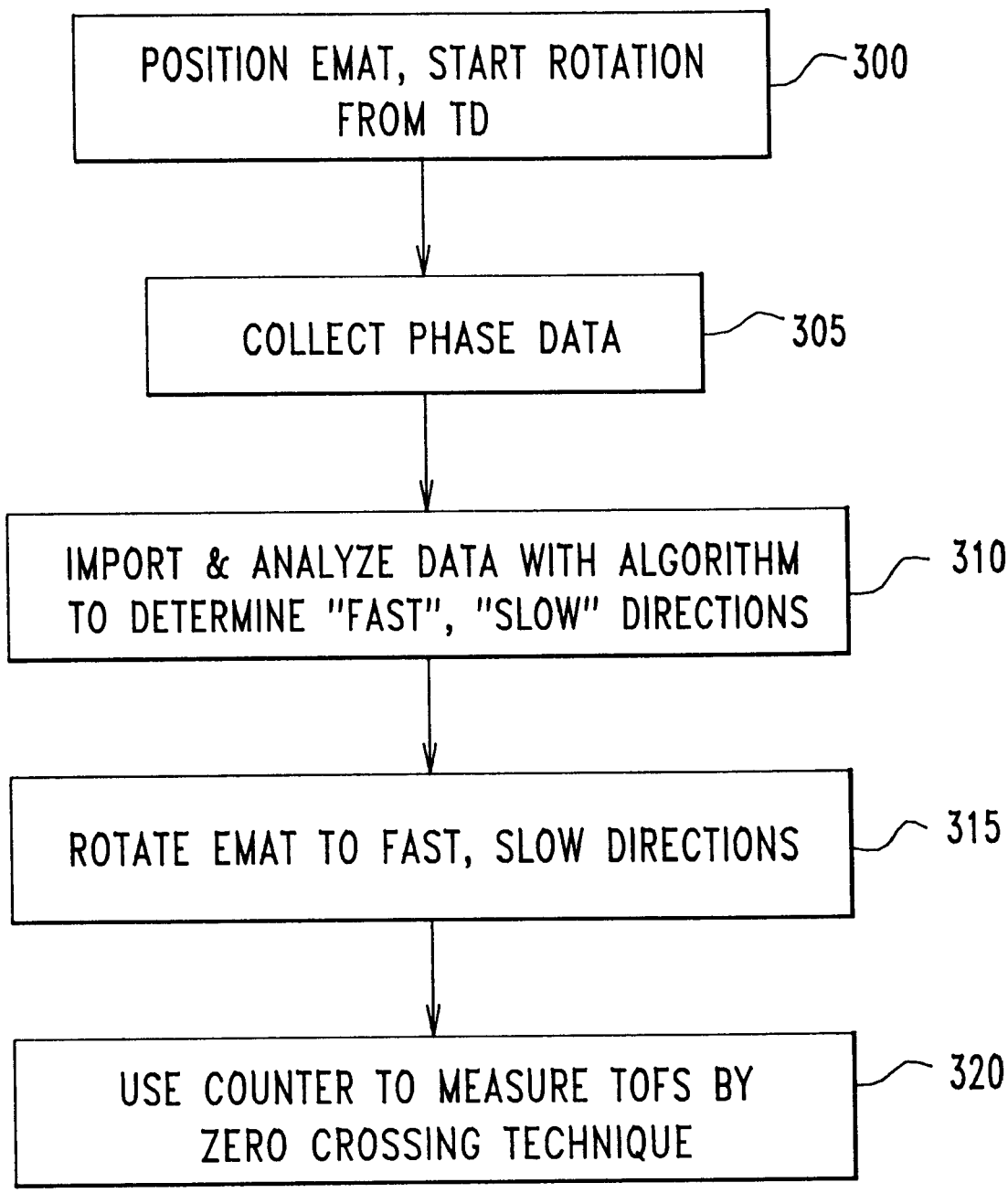
FIG. 9 shows a flowchart of the measurement process for the hybrid system.

FIG. 9 shows a flowchart of the measurement process for the hybrid system. The EMAT is positioned at the measurement location and is rotated, block 300. The phase data is then measured and recorded by the commercial instrument, block 305. The angle Φ is determined with the algorithm, block 310. The EMAT is then rotated along the "fast" and "slow" directions, block 315, and the corresponding TOFs measured with the counter, block 320.

Demonstration of Accuracy of Stress Measurements

Figure 10:
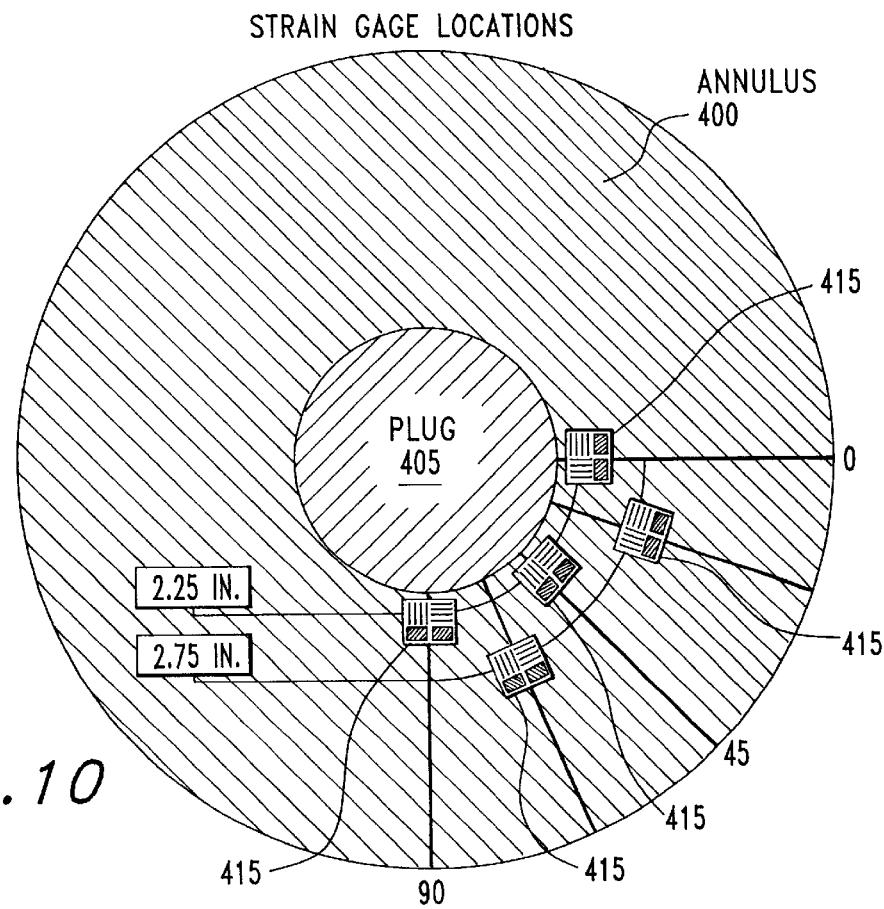
FIG. 10 shows the specimen along with the strain gage layout.

FIG. 10 shows the specimen along with the strain gage layout. In order to demonstrate the accuracy of the method, a specimen having known stresses was constructed. The data obtained by strain gages, 415, and the ultrasonic method was compared. The specimen consists of an outer annulus 400 and an inner plug 405. The plug diameter is slightly larger then the inner diameter of the annulus. The annulus is heated and the plug cooled (to obtain the necessary clearance) and the plug is then inserted into the annulus, resulting in an interference fit. On reaching ambient temperature a state of compressive radial stress and tensile hoop stress a results.

A general functional form (with unknown coefficients) has been developed that satisfies stress equilibrium. The unknown coefficients are determined from a least-squares fit to the strain gage data. It is then possible to predict the stresses at all locations in the specimen.

Figure 11:
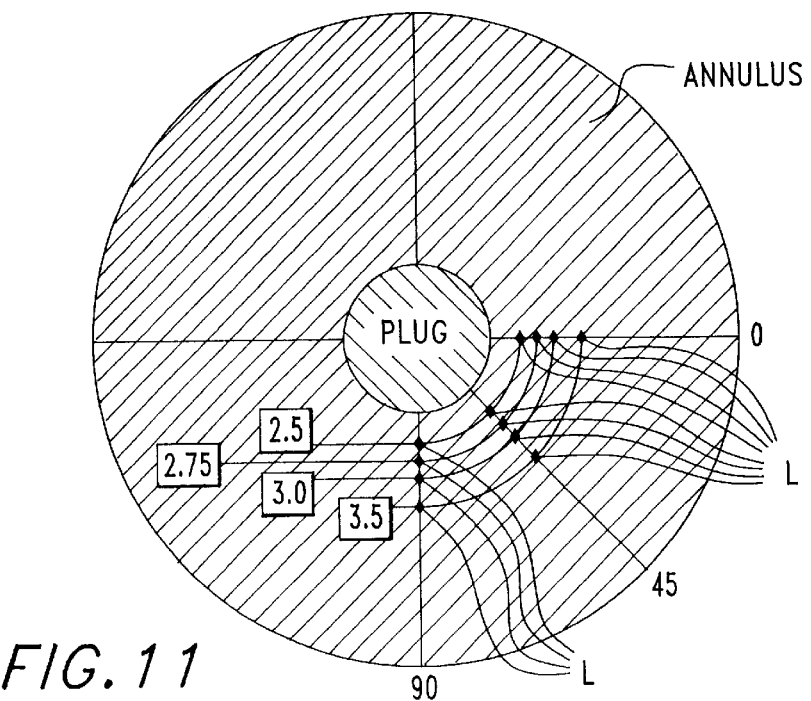
FIG. 11 shows the 12 locations where ultrasonic measurements of Φ and TOF were done at before and after assembly of the component.

FIG. 11 shows the locations, L, of ultrasonic measurements of Φ and TOF taken at the 12 locations before and after assembly of the component. The data were used with the same functional form to determine the unknown coefficients (which are slightly different from those determined from the strain gage data). Hence, one can predict stresses at all locations in the specimen based on the ultrasonic data.

Figure 12:
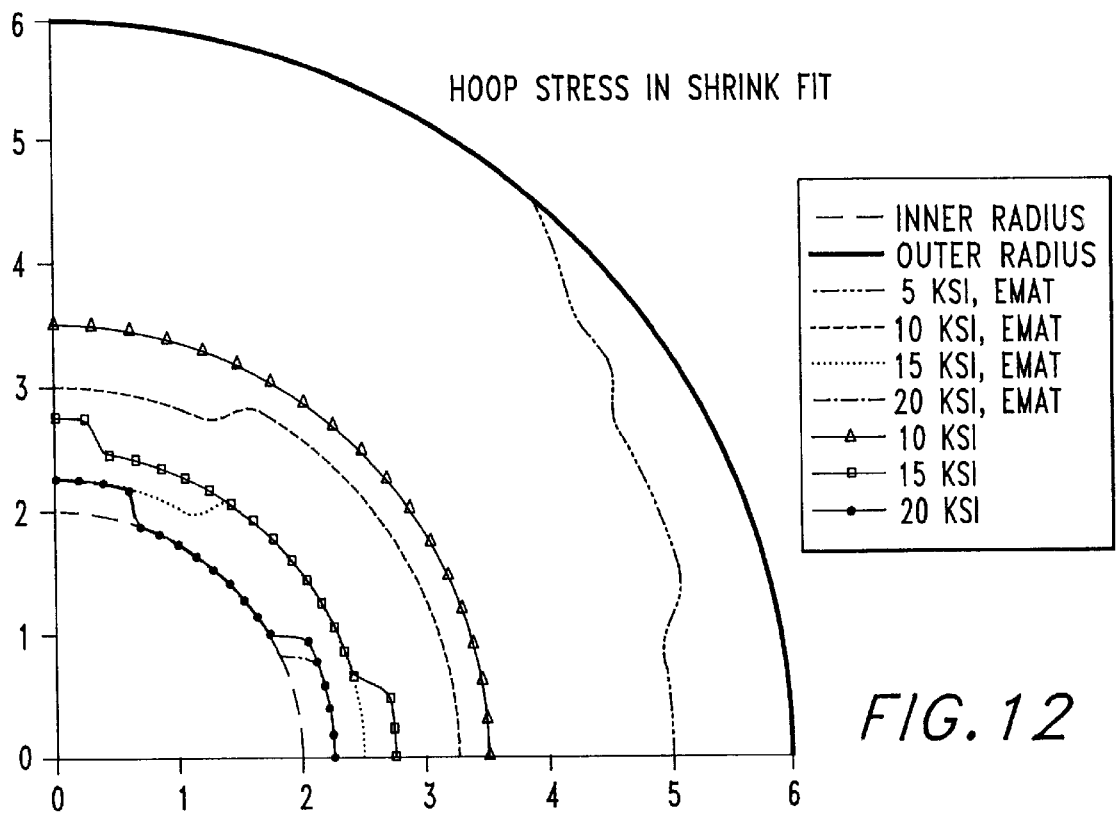
FIG. 12 shows contours of radial hoop stress plotted based on results of strain gage and ultrasonic measurements.

FIG. 12 shows contours of radial hoop stress plotted based on results of strain gage and ultrasonic measurements.

Figure 13:
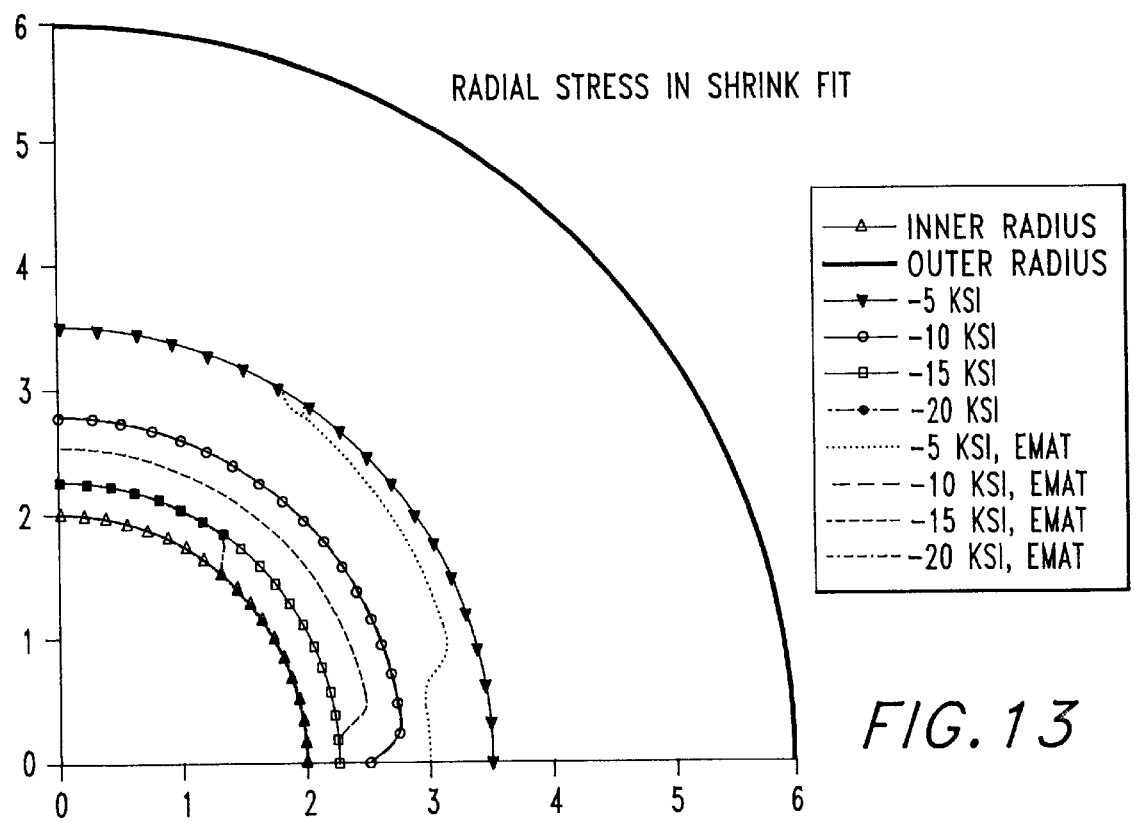
FIG. 13 shows the corresponding results for the radial stress.

FIG. 13 shows the corresponding results for the radial stress. The data appears to have "jumps" because in the fitting routine locations of stress contours are resolved to the nearest 6.3 mm (0.25 inch)).

Figure 14:
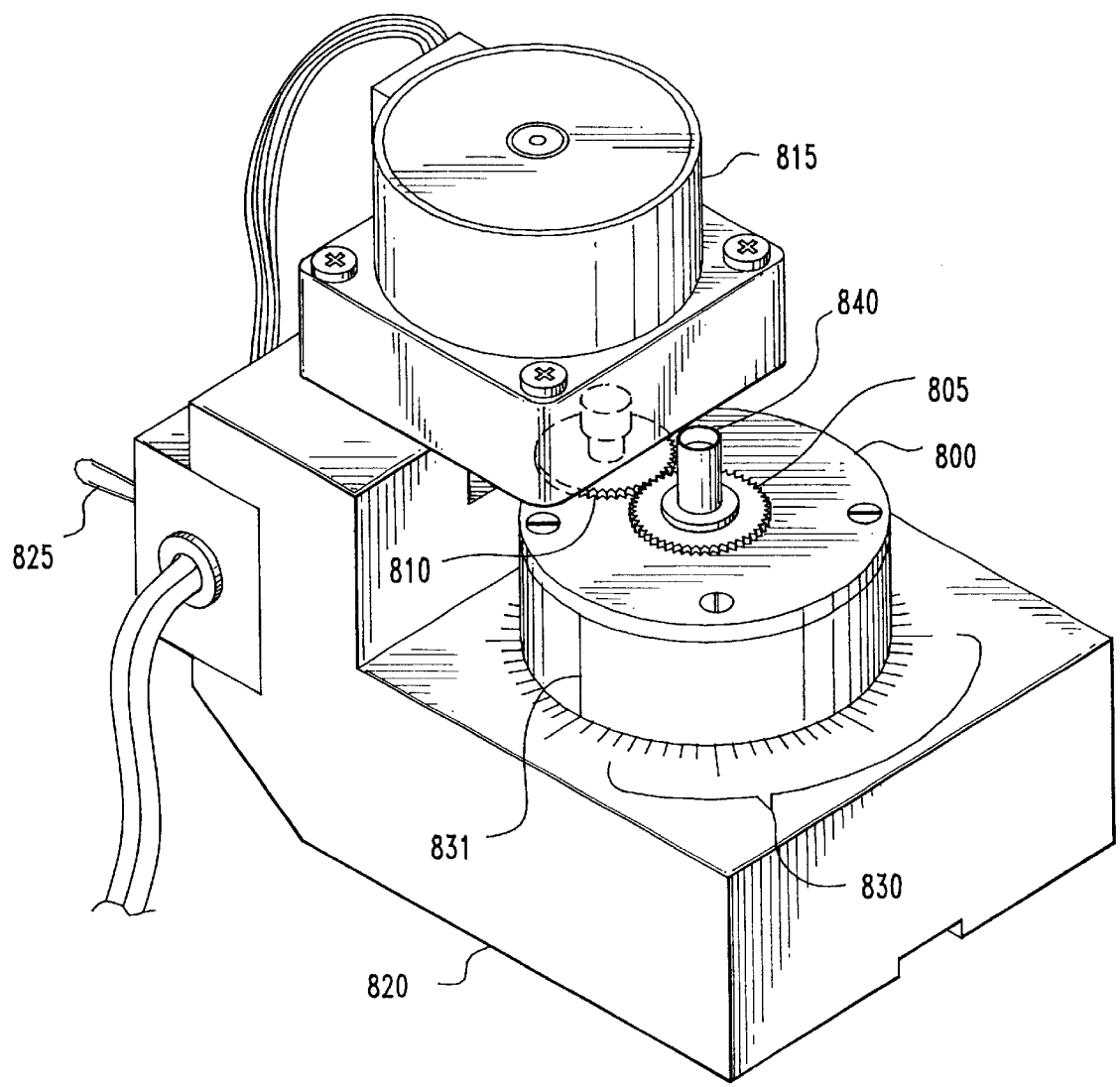
FIG. 14 is a top perspective view of the preferred embodiment showing the drive mechanism.

FIG. 14 is a top perspective view of the preferred embodiment showing the EMAT with drive mechanism. EMAT 800 is as described in FIG. 4. It is mounted in base 820. Gear 805 on EMAT 800 meshes with gear 810 on motor 815. Motor 815 is also mounted to base 820. Signal cable (not shown) from the diplexer 120 is connected to EMAT at coax connector 840. EMAT position information may be visually obtained from the scale 830 and reference mark 831, to which the EMAT is indexed as described above.

In an alternate embodiment, a digital encoder is used to determine the angular position of the EMAT. The position data obtained from the digital encoder is used to determine the EMAT orientation η. In lieu of the gear train shown in FIG. 14, a drive chain is used to connect the motor to the EMAT shaft.

Although the present invention has been described with reference to preferred embodiments, numerous modifications and variations can be made and still the result will come within the scope of the invention. No limitation with respect to the specific embodiments disclosed herein is intended or should be inferred.

We claim:

1. An ultrasonic strain gauge comprising:
   a computer;
   an instrument for generating a signal;
   an oscilloscope;
   an electromagnetic acoustic transducer (EMAT);
   a digital gate;
   a counter;
   a diplexer;
   said computer controlling said instrument, oscilloscope, EMAT, digital gate, counter and diplexer;
   said instrument connected to said diplexer and to said digital gate and to said oscilloscope, whereby a signal generated by said instrument is transmitted and received by said instrument;
   said instrument connected to said counter and to a switch;
   said digital gate connected to said switch and to said oscilloscope and to said counter whereby a signal is captured from said EMAT for analysis;
   said counter connected to said digital gate and to said instrument whereby a zero crossing for a signal is identified;
   said diplexer connected to said EMAT for selecting signals transmitted to and from said EMAT;
   wherein said computer compares a first time of flight (TOF) and a second TOF and determines an orientation of pure mode polarization directions $\Phi$ of a specimen in a stressed state, where $\Phi$ is an angle of rotation from pure mode polarization directions;
   wherein said first TOF is measured from a signal transmitted to and from said EMAT to select a zero crossing in the signal; and
   wherein said second TOF is measured from a second signal transmitted to and from said EMAT to select a zero crossing in said second signal.

2. The ultrasonic strain gauge as in claim 1, wherein said computer further comprises:
   a memory for storage of data; and
   a visual display for viewing of results by a user.

3. The ultrasonic strain gauge as in claim 2, wherein said electromagnetic acoustic transducer further comprises:
   a coil and a magnet contained within a rotating cylinder;
   an outer case containing said rotating cylinder in an inner area;
   a bearing fixed between said rotating cylinder and said outer case whereby said rotating cylinder may freely rotate within said outer case; and
   a magnetic plate fixed to a first end of said outer case.

4. An apparatus for measurement of stress in a specimen, the apparatus comprising:
   means for placing a rotating EMAT at a first location on a specimen functioning to generate and receive wave signals to determine TOF in the unstressed state at a known angle $\eta$, said specimen being in an unstressed state;
   means for controlling said rotating EMAT to emit a first toneburst which creates shear horizontal SH waves in said specimen functioning to prepare to measure a return echo signal;
   means for measuring a phase of the return echo signal from said specimen functioning in calculating the birefringence from the normalized differences in the phase of the SH wave;
   means for measuring a first time of flight (TOF) from said received signal echo to select a zero crossing in the signal echo;
   means for storing said first TOF and determining an orientation of pure mode polarization directions $\Phi$ of the specimen, where $\Phi$ is an angle of rotation from pure mode polarization directions;
   means for inducing a stressed state in said specimen; said stressed state having a $\sigma_{xx}$ component, a $\sigma_{yy}$ component and a $\sigma_{xy}$ component;
   means for using said rotating EMAT at the first location at a later time on said specimen, causing said rotating EMAT to emit a second toneburst functioning to determine a change in stress in the specimen at the later time;
   means for measuring a phase of a second received signal echo from said specimen functioning to calculate birefringence from the normalized differences in the phase of the SH wave;
   means for measuring a second time of flight (TOF) from said second received signal to select a zero crossing in the second signal echo;
   means for comparing said first TOF and said second TOF and means for determining an orientation of pure mode polarization directions $\Phi$ of the specimen in the stressed state, where $\Phi$ is an angle of rotation from pure mode polarization directions; and
   means for calculating a change in stress component $\sigma_{xx}$, stress component $\sigma_{yy}$, and stress component $\sigma_{xy}$ in said specimen using $\Phi$ and the first and second TOF's for the unstressed state and for the stressed state, respectively.

5. The apparatus of claim 4 further comprising means for rotating said rotating EMAT with a motor controlled by a computer functioning to fix the EMAT at known positions.

6. The apparatus of claim 5 further comprising means for mounting said rotating EMAT to the specimen by a magnetic connector.

7. The apparatus of claim 6 further comprising means for storing said first TOF and said second TOF in a computer storage media functioning to allow measurement in a change of TOF at different points in time.

8. The apparatus of claim 7 further comprising means for displaying the change in stress components $\sigma_{xx}$, $\sigma_{yy}$, $\sigma_{xy}$ on a visual display device.

9. The apparatus of claim 5 further comprising means for coupling said motor to said rotating EMAT with a gear drive functioning to control the rotation of the EMAT.

10. The apparatus of claim 5 further comprising means for coupling said motor to said rotating EMAT with a chain drive functioning to control the rotation of the EMAT.

11. The apparatus of claim 5 further comprising:
    means for receiving a SH-wave generated by said rotating EMAT in said specimen; said SH-wave having an x and y component with amplitude $\sin \theta$ and $\cos \theta$, respectively for various values of $\theta$, where $\theta$ is an angle of rotation of said rotating EMAT from an acoustic axis in said specimen in an unstressed state, effected by rotating said rotating EMAT with said motor on said specimen;
    means for calculating a particle velocity U from the equation:

$$U^2 \sim \exp(j\ P_{ave}) \ \{\cos^2\theta \exp(j\ \Delta P) + \sin^2\theta \exp(-j\Delta P)\}$$

Where:

~means "proportional to"
j=√−1
$P_{ave}$=average phase
θ=angle of rotation from the acoustic axis
$\Delta P = P_s - P_f$, the difference in phase between SH wave components in slow and fast directions;

means for calculating a synthetic phase ψ syn (η;Φ*) for various values of θ from the equation:

$$\psi syn\ (\eta;\Phi^*) = \arctan\{\tan^{-1}(\Delta P/2)\cos 2(\eta-\Phi^*)\};$$

Where:
$\Delta P = \psi_{max} - \psi_{min}$
$\psi_{max}$=maximum phase
$\psi_{min}$=minimum phase
η=Angle of rotation from pure mode polarization direction in the unstressed state
Φ*=assumed value of Φ the angle of rotation of the pure mode polarization directions;

means for calculating a residual R (Φ*) for various assumed values of Φ from the following equation:

$$R(\Phi^*) = \Sigma(\psi_{syn}(\eta_i;\Phi^*) - \psi(\eta_i;\Phi^*))$$

Where:
$\psi_{syn}$=synthetic phase
ψ=phase measured by rotating EMAT
$\eta_i = wt_i$
w=angular velocity of rotating EMAT
$t_i = i_{th}$ increment of clock time means for searching the calculated values of the residual to determine Φ at the minimum residual value;
means for measuring times of flight with said rotating EMAT oriented at Φ and Φ+90°, where Φ is determined at the minimum residual value;
means for repeating the above procedure with said specimen in a stressed state to determine Φ, and times of flight with said rotating EMAT oriented at Φ and Φ+90°, where Φ is determined at the minimum residual value; and
means for calculating a change of stress using the following equation:

$$\Delta\sigma_{xx} = K_{11}\Delta\tau_1 + K_{12}\Delta\tau_2.$$

$$\Delta\sigma_{yy} = K_{21}\Delta\tau_1 + K_{22}\Delta\tau_2.$$

$$\Delta\sigma_{xy} = K_{33}\Delta\tau_3$$

Where:
$K_{12}$, etc. are=acoustoelastic constants $\Delta\tau_i$=difference in $\tau_I$ in unstressed and stressed states
Where:

$$\tau_1 = (T_s\cos^2\Phi + T_f\sin^2\Phi)/T_o;$$

$$\tau_2 = (T_f\cos^2\Phi + T_s\sin^2\Phi)/T_o;$$

$$\tau_3 = [(T_s - T_f)\sin^2 2\Phi]/2T_o$$

Where:
$T_s$=Time of flight of wave polarized in slow direction
$T_f$=Time of flight of wave polarized in fast direction
$T_o$=Average time of flight
Φ=Angle between the pure mode directions in the unstressed and stressed states.

12. The apparatus of claim 5 further comprising means for coupling an input/output cable to a computer during rotation of the EMAT functioning to prevent a twisting of cables.

* * * * *